United States Patent [19]

DeVries et al.

[11] Patent Number: 4,945,158

[45] Date of Patent: Jul. 31, 1990

[54] ANTIDIABETIC PHOSPHONATES

[75] Inventors: Vern G. DeVries, Ridgewood; Thomas H. Claus, Montvale, both of N.J.; Middleton B. Floyd, Jr., Suffern; Semiramis Ayral-Kaloustian, Tarrytown, both of N.Y.

[73] Assignee: American Cyanamid Company, Stamford, Conn.

[21] Appl. No.: 232,333

[22] Filed: Aug. 12, 1988

[51] Int. Cl.$^5$ .............................................. C07H 11/04
[52] U.S. Cl. ...................................... 536/117; 514/25
[58] Field of Search ...................... 536/117; 514/24, 25

[56] References Cited

U.S. PATENT DOCUMENTS 4,745,185  5/1988  Maryanoff et al. ................. 536/117

OTHER PUBLICATIONS

Rabinsohn et al., J. Org. Chem., 32, 3452–3257 (1967).
Koerner et al., Carbohydrate Res., 59, 403–416 (1977).
Pilkis et al., J. Biol. Chem., 256, 3171–3174 (1981).
Voll et al., Carbohydrate Res., 95, 145–154 (1981).
Otero et al., Carbohydrate Res., 128, 79–86 (1984).
McClard et al., Arch. Biochem. & Biophys., 245, 282–286 (1986).
Meuwly, Helv. Chim. Acta, 69, 751–760 (1986).
Nicotra et al., J. Org. Chem., 52, 5627–5630 (1987).
Reitz et al., Tetrahedron Letters, 26, 3915–3918 (1985).
Maryanoff et al., Carbohydrate Res., 171, 295-278 (1987).
Hanson et al., The Journal of Biological Chemistry, Inhibition of Gluconeogenesis and Glycogenolysis by 2,5-Anhydro-D-Mannitol, vol. 259, No. 1, Jan. 10, pp. 218–223, 1984.
The British Drug Houses Ltd., "Sugar Phosphates and Some Closely Related Substances", Mar. 1958, p. 5.

*Primary Examiner*—Ronald W. Griffin
*Attorney, Agent, or Firm*—Alan M. Gordon

[57] ABSTRACT

Phosphonates are disclosed which stimulate the enzyme fructose-1,6-bisphosphatase and inhibit the enzyme 6-phosphofructo-1-kinase, thereby lowering glucose levels in mammals. These phosphonates may thus be used to treat hyperglycemia and/or diabetes. Processes for the synthesis of the phosphonates are also disclosed.

17 Claims, No Drawings

ANTIDIABETIC PHOSPHONATES

BACKGROUND OF THE INVENTION

This invention relates to novel organic compounds which are useful as pharmaceutical agents. The novel compounds of this invention modulate the activity of enzymes which control the processes of glycolysis and gluconeogenesis, two processes which help to regulate blood glucose levels in mammals. As such, the compounds of the present invention are useful for treating hyperglycemia and/or diabetes in warm-blooded animals. This invention also relates to methods for treating hyperglycemia and/or diabetes in mammals in need of such treatment, to pharmaceutical compositions for the utilization of these novel compounds in the treatment of hyperglycemia and/or diabetes and to processes for the chemical syntheses of these compounds.

The disease diabetes mellitus, commonly referred to as diabetes, is characterized by metabolic defects in the production and disposal of glucose. The result of these defects is the inability to maintain appropriate blood glucose (or blood sugar) levels. Treatments of diabetes have commonly employed the administration of exogenous insulin, the oral administration of drugs, or the use of dietary therapy. Initially it was believed that the hyperglycemia observed in diabetics was simply the result of a deficiency in the supply of insulin, the principal hormone which controls glucose metabolism. As a result, research focused on the source of insulin production, the beta cells of the pancreas, and pharmaceutical agents which stimulated these cells to release insulin were developed.

Although it is true that a deficiency in insulin production can produce hyperglycemia, it has now been recognized that a variety of defects in metabolic processes can play a major role in the control of blood glucose levels. Metabolic processes which are important in this regard include glycolysis (the metabolic degradation of glucose to lactic acid), gluconeogenesis (the metabolic process by which endogenous synthesis of glucose from lactic acid occurs), glycogenolysis (the metabolic process by which glucose is released from stored glycogen), and insulin stimulated glucose uptake (the metabolic process by which peripheral tissues acquire glucose as an energy source). Defects in any or all of these metabolic processes have significant effects on the maintenance of appropriate blood glucose levels.

In Type I diabetes, also called juvenile-onset or insulin-dependent diabetes, a deficiency in insulin production is the major cause of hyperglycemia. However, the majority of diabetics suffer from a form of the disease referred to as Type II, also called maturity-onset or non-insulin-dependent diabetes. In most Type II diabetics, basal insulin levels are normal or even elevated; in spite of this, transient or continuous elevations in blood glucose levels occur. In such disease states, the metabolic processes mentioned above, which normally function to provide exquisite control over blood glucose levels, are operating in an aberrant manner. Thus, a pharmaceutical agent capable of regulating these processes would be useful in restoring normal metabolic control of blood sugar levels.

Two of the above-described metabolic processes which are vitally important to glucose homeostasis are glycolysis and gluconeogenesis. In the process called glycolysis, glucose is converted in a series of enzymatically catalyzed transformations to lactic acid. In the process called gluconeogenesis, glucose is synthesized from lactic acid in another series of enzymatically catalyzed transformations. It is well known that proper regulation of these two metabolic processes is essential for the maintenance of appropriate blood glucose levels.

In recent years research has resulted in the discovery of a natural product, beta-D-fructose-2,6-bisphosphate (Pilkis et al., *J. Biol. Chem.*, 256, 3171–3174 (1981)), which has now been demonstrated to be an important regulator of both glycolysis and gluconeogenesis. Beta-D-fructose-2,6-bisphosphate exerts its regulatory action on these metabolic processes by specifically modulating the activity of a key enzyme involved in each of these processes. First, beta-D-fructose-2,6-bisphosphate promotes glycolysis by stimulating the enzyme 6-phosphofructo-1-kinase, which catalyzes the conversion of fructose-6-phosphate to fructose-1,6-bisphosphate. Second, beta-D-fructose-2,6-bisphosphate attenuates gluconeogenesis by inhibiting the enzyme fructose-1,6-bisphosphatase, which catalyzes the conversion of fructose-1,6-bisphosphate to fructose-6-phosphate. Either or both of these regulatory actions serve to reduce glucose levels, the former by promoting the metabolic degradation of glucose and the latter by attenuating the endogenous synthesis of glucose. Thus, the net result of the regulatory action of beta-D-fructose-2,6-bisphosphate is a lowering of glucose levels, the exact result desired in the treatment of hyperglycemic and/or diabetic states.

It has now been found that the novel organic compounds of the present invention exert regulatory actions on the key enzymes of the glycolytic and gluconeogenic processes in the same manner as the natural product, beta-D-fructose-2,6-bisphosphate. The novel compounds are more resistant to enzymatic or hydrolytic degradation than the natural product, which has a labile acetal phosphate group. The novel compounds are stimulators of the enzyme 6-phosphofructo-1-kinase and inhibitors of the enzyme fructose-1,6-bisphosphatase; the net result of these actions being the lowering of glucose levels. As such, they are useful for the treatment of hyperglycemic and/or diabetic states in mammals.

SUMMARY OF THE INVENTION

This invention relates to novel organic compounds of the formula:

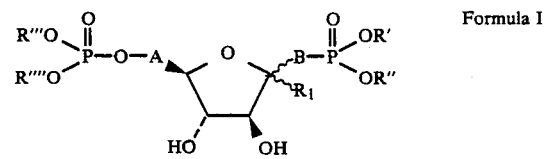

Formula I wherein A and B are selected independently of each other from the group consisting of $C_1$ to $C_4$ alkylene and $C_2$ to $C_4$ hydroxyalkylene; $R_1$ is selected from the group consisting of hydrogen, hydroxy, $C_1$ to $C_4$ alkyl, $C_1$ to $C_4$ hydroxyalkyl, $C_2$ to $C_4$ dihydroxyalkyl, $C_3$ or $C_4$ trihydroxyalkyl and $C_4$ tetrahydroxyalkyl; R', R'', R''' and R'''' are selected independently from the group consisting of hydrogen, $C_1$ to $C_{18}$ alkyl, $C_3$ to $C_6$ cycloalkyl, phenyl, mono- and disubstituted phenyl (wherein the substituents are selected from alkyl $C_1$ to $C_6$, alkoxy $C_1$ to $C_6$, nitro or halo), $C_3$ to $C_8$ isoalkyl, $Cl_3CCH_2$—, $CH_2=CHCH_2$—, $ZCH_2CH_2$— (where Z is $SO_2R_2$, $SR_2$, $OR_2$ or $Si(R_2)_3$ and $R_2$ is $C_1$ to $C_3$ alkyl),

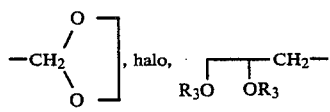, halo,

[where $R_3$ is $C_1$ to $C_3$ alkyl and $R_3$-$R_3$ is alkylene or acetal],

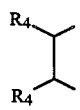

(where $R_4$ is hydrogen or methyl),

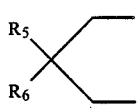

[where when $R_5 = R_6$ they are both hydrogen, fluoro or $C_1$ to $C_4$ alkyl, $R_5$=hydrogen, $R_6$=fluoro, hydroxy or $OR_7$ (where $R_7 = C_1$ to $C_6$ alkyl, $C_3$ to $C_6$ cycloalkyl or aryl)],

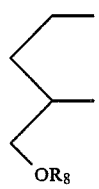

where $R_8$ is hydrogen or $C_1$ to $C_{18}$ alkyl,

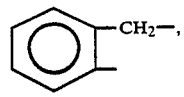

phenylmethyl, substituted phenylmethyl wherein the substituents are selected from $C_1$ to $C_{18}$ alkyl, $C_1$ to $C_6$ alkoxy, nitro and halogen; and with the provisos that (a) when A and B are both —$CH_2$— and R', R", R''' and R'''' are the same and are phenyl or ethyl, then $R_1$ may not be hydrogen, and (b) when A and B are both —$CH_2$— and R', R", R''' and R'''' are hydrogen, then $R_1$ may not be hydrogen or —$CH_2OH$; and, when any one or more of R', R", R''' or R'''' are hydrogen, the pharmaceutically acceptable salts thereof.

This invention also relates to methods for treating hyperglycemia and/or diabetes in mammals in need of such treatment, and to pharmaceutical compositions containing the compounds of the above formula without the provisos and to the chemical syntheses of these compounds.

DETAILED DESCRIPTION OF THE INVENTION

Compounds of the present invention may be prepared according to the following flowchart. In these flowcharts, the phenyl group

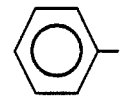

is abbreviated Ph.

Flowchart A

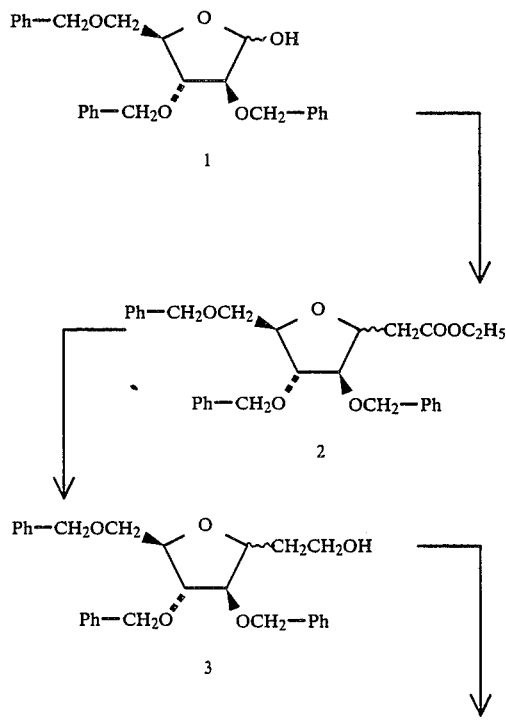

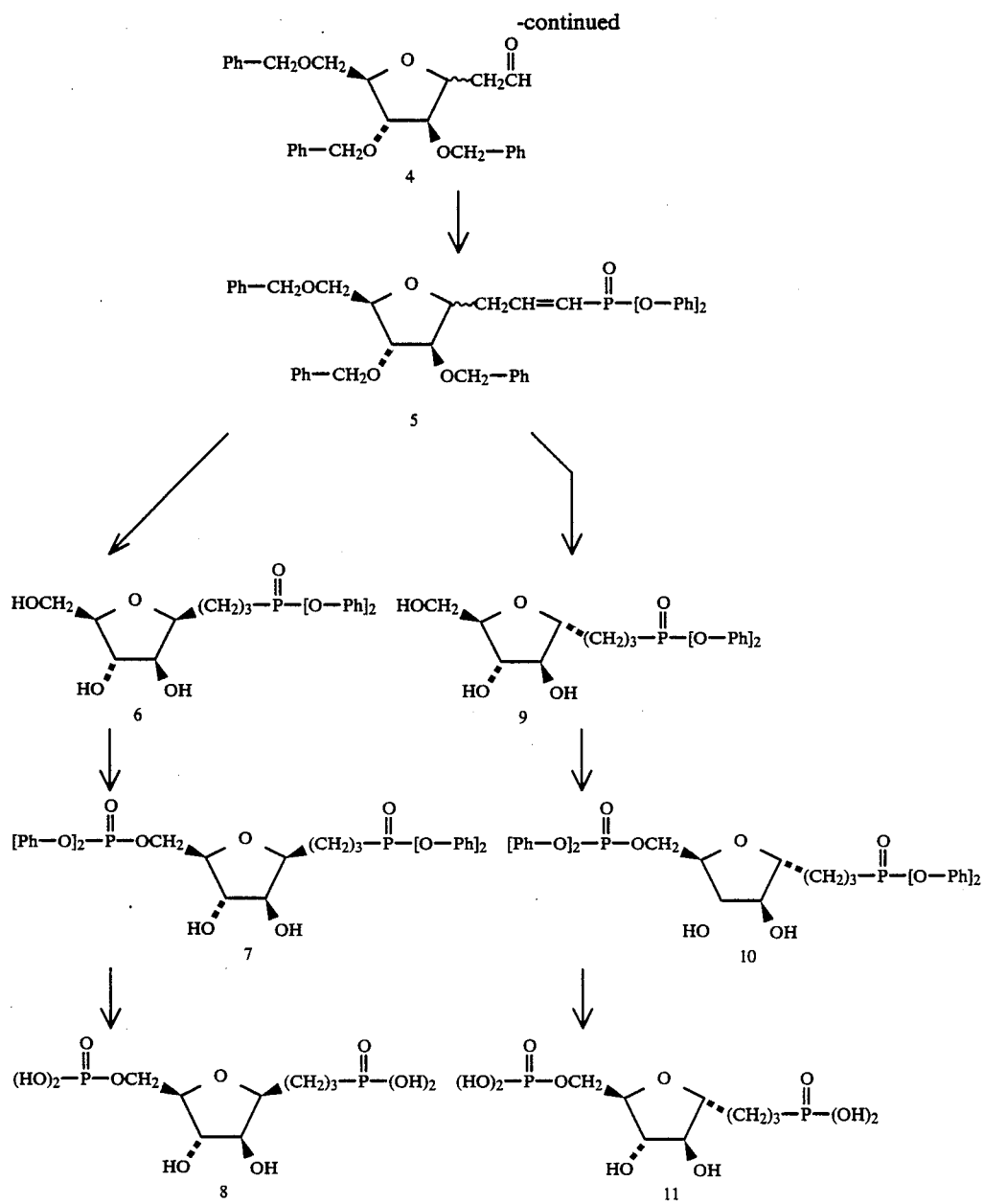

According to Flowchart A, 2,3,5-tris-O-(phenylmethyl)-D-arabinofuranose (Sigma Chemical Co.), 1, is treated with the phosphonate carbanion prepared by reacting sodium hydride and triethylphosphonoacetate in dimethoxy ethane, giving 2,3-dideoxy-4,5,7-tris-O-(phenylmethyl)-D-arabino-3-heptulo-3,6-furanosonic acid, ethyl ester, 2, which is reacted with lithium aluminum hydride in ether giving mixture 3. This is reacted with a solution of chromium trioxide and pyridine in dichloromethane under an inert atmosphere, giving 3,6-anhydro-2-deoxy-4,5,7-tris-O-(phenylmethyl)-D-gluco(and D-manno)-heptose as a mixture 4. The epimeric mixture, 4, is reacted with diphenyl triphenylphosphoranylidenemethylphosphonate in toluene at reflux, giving 4,7-anhydro-1,2,3-trideoxy-1-(diphenoxyphosphinyl)-5,6,8-tris-O-(phenylmethyl)-D-gluco(and D-manno)-oct-1-enitol as a mixture 5. Mixture 5 is hydrogenated in methanol and glacial acetic acid using palladium on carbon catalyst and then the alpha and beta isomers are separated by flash chromatography giving 4,7-anhydro-1,2,3-trideoxy-1-(diphenoxyphosphinyl)-D-gluco-octitol, 6 (the beta isomer) and the corresponding D-manno-octitol, 9. The beta isomer, 6, is then reacted with diphenyl chlorophosphate in pyridine at ice bath temperature, giving the product 4,7-anhydro-1,2,3-trideoxy-1-(diphenoxyphosphinyl)-D-gluco-octitol, 8-(diphenyl phosphate), 7, which is then hydrogenated in methanol with platinum oxide catalyst, giving the product 4,7-anhydro-1,2,3-trideoxy-1-(dihydroxyphosphinyl)-D-gluco-octitol, 8-(dihydrogen phosphate) 8.

The alpha isomer, 9, gives the product 4,7-anhydro-1,2,3-trideoxy-1-(diphenoxyphosphinyl)-D-manno-octitol, 8-(diphenylphosphate), 10, and the product 4,7-anhydro-1,2,3-trideoxy-1-(dihydroxyphosphinyl)-D-manno-octitol, 8-(dihydrogen phosphate) 11, as described above.

Flowchart B
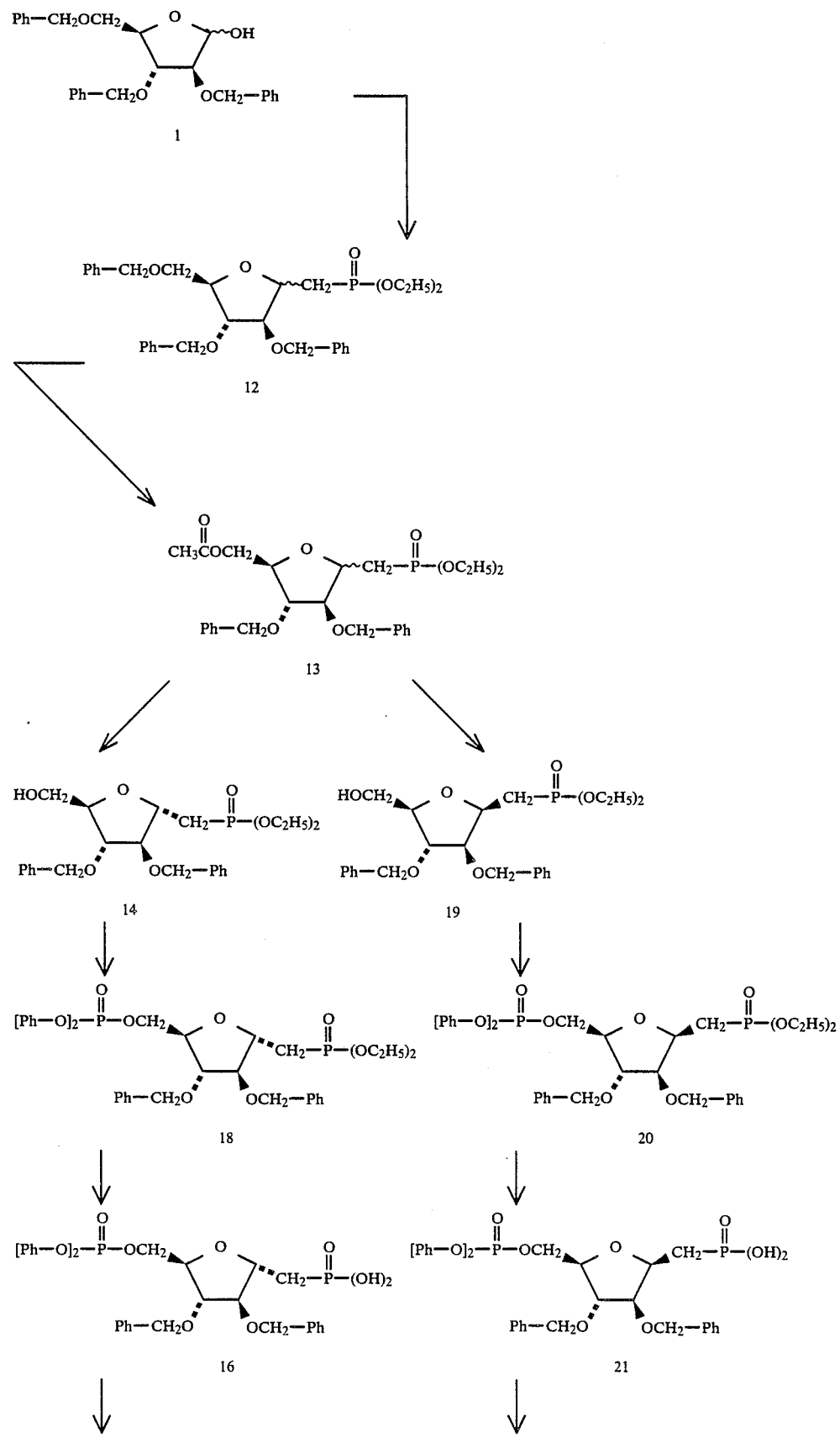

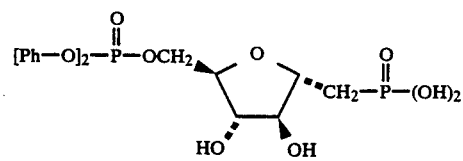

17

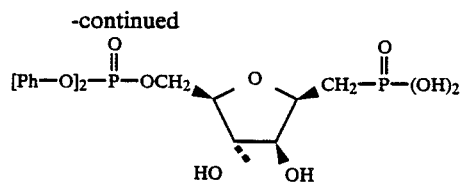

22

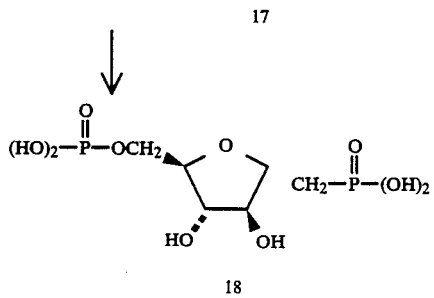

18

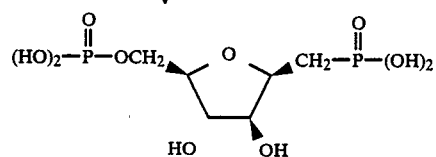

23

According to Flowchart B, 2,3,5-tris-O-(phenylmethyl)-D-arabinofuranose 1 is reacted with tetraethylmethylenebisphosphonate and sodium hydride in dimethoxyethane, giving 2,5-anhydro-1-deoxy-1-(diethoxyphosphinyl)-3,4,6-tris-O-(phenylmethyl)-D-glucitol and D-mannitol mixture 12, which is then selectively acetolyzed with acetic anhydride and boron trifluoride etherate, giving 2,5-anhydro-1-deoxy-1-(diethoxyphosphinyl)-3,4-bis-O-(phenylmethyl)-D-glucitol and D-mannitol, 6-(acetate) as mixture 13. Mixture 13 is reacted with sodium ethoxide in ethanol, giving, after separation by flash chromatography, 2,5-anhydro-1-deoxy-1-(diethoxyphosphinyl)-3,4-bis-O-(phenylmethyl)-D-mannitol 14 (the alpha isomer) and the corresponding D-glucitol, 19 (the beta isomer). The isomers, 14 and 19 are individually reacted with diphenyl chlorophosphate in pyridine, giving 2,5-anhydro-1-deoxy-1-(diethoxyphosphinyl)-3,4-bis-O-(phenylmethyl)D-mannitol, 6-(diphenyl phosphate), 15, and the D-glucitol isomer 20 which are then dealkylated with trimethylsilyl bromide in dichloromethane under an inert atmosphere, giving 2,5-anhydro-1 -deoxy-3,4-bis-O-(phenylmethyl)-1-phosphono-D-mannitol, 6-(diphenyl phosphate), 16 and the D-glucitol isomer 21. Compounds 16 and 21 are hydrogenated with palladium on carbon in methanol, giving 2,5-anhydro-1-deoxy-1-phosphono-D-mannitol, 6-(diphenyl phosphate) 17 and the D-glucitol isomer 22, which are further hydrogenated with platinum oxide catalyst, giving the products 2,5-anhydro-1-deoxy-1-phosphono-D-mannitol, 6-(dihydrogen phosphate) 18 and 2,5-anhydro-1-deoxy-1-phosphono-D-glucitol, 6-(dihydrogen phosphate) 23. Compound 18 is disclosed in A. B. Reitz et al., *Tetrahedron Letters*, 26, 3915-3916 (1985), while compound 23 is disclosed in Reitz et al. (supra) and R. W. McClard et al., *Archives of Biochem & Biophys.*, 245, 282-286 (1986). However, the compounds are prepared by processes which differ from those disclosed in this application.

Flowchart C

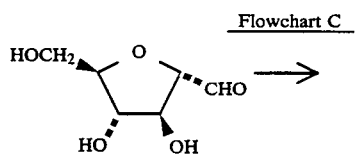

24

-continued
Flowchart C

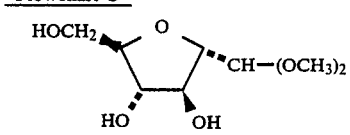

25

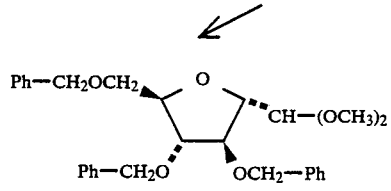

26

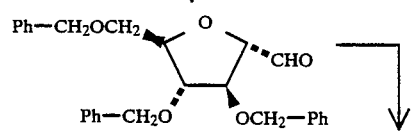

27

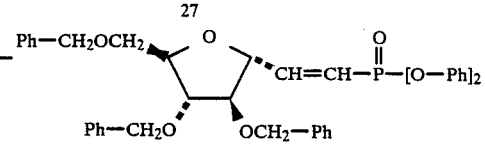

28

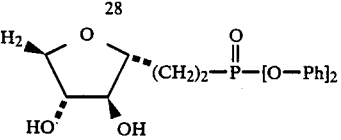

29

-continued
Flowchart C

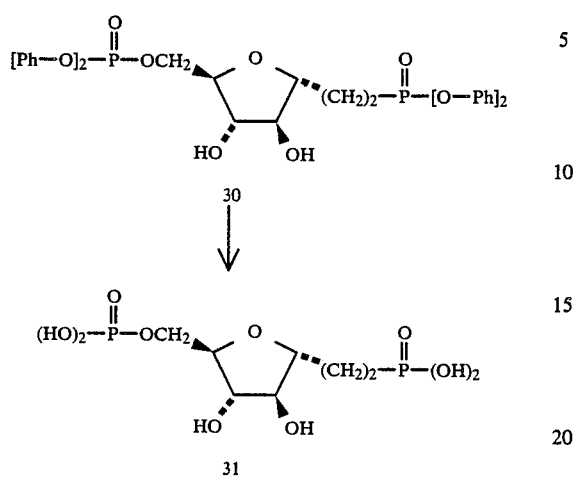

According to Flowchart C, 2,5-anhydro-D-mannose 24, is protected as the dimethyl acetal 25 which is reacted with sodium hydride in dimethylformamide, followed by benzyl bromide giving 2,5-anhydro-3,4,6-tris-O-(phenylmethyl)-D-mannose, dimethyl acetal 26. Compound 26 is treated with tetrafluoroboric acid in acetonitrile giving 2,5-anhydro-3,4,6-tris-O-(phenylmethyl)-D-mannose 27 which is reacted with diphenyl triphenylphosphoranylidenemethylphosphonate in toluene at reflux, giving 3,6-anhydro-1,2-dideoxy-1-(diphenoxyphosphinyl)-4,5,7-tris-O-(phenylmethyl)-D-manno-hept-1-enitol 28. Compound 28 is hydrogenated over palladium on carbon in methanol and acetic acid, giving 3,6-anhydro-1,2-dideoxy-1-(diphenoxyphosphinyl)-D-manno-heptitol 29, which is reacted with diphenyl chlorophosphate in pyridine, giving 3,6-anhydro-1,2-dideoxy-1-(diphenoxyphosphinyl)-D-manno-heptitol, 7-(diphenyl phosphate) 30, which is then hydrogenated with platinum oxide, giving the product 3,6-anhydro-1,2-dideoxy-1-phosphono-D-manno-heptitol, 7-(dihydrogen phosphate) 31.

Flowchart D

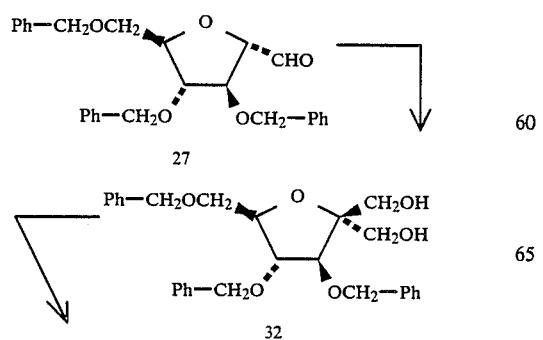

-continued
Flowchart D

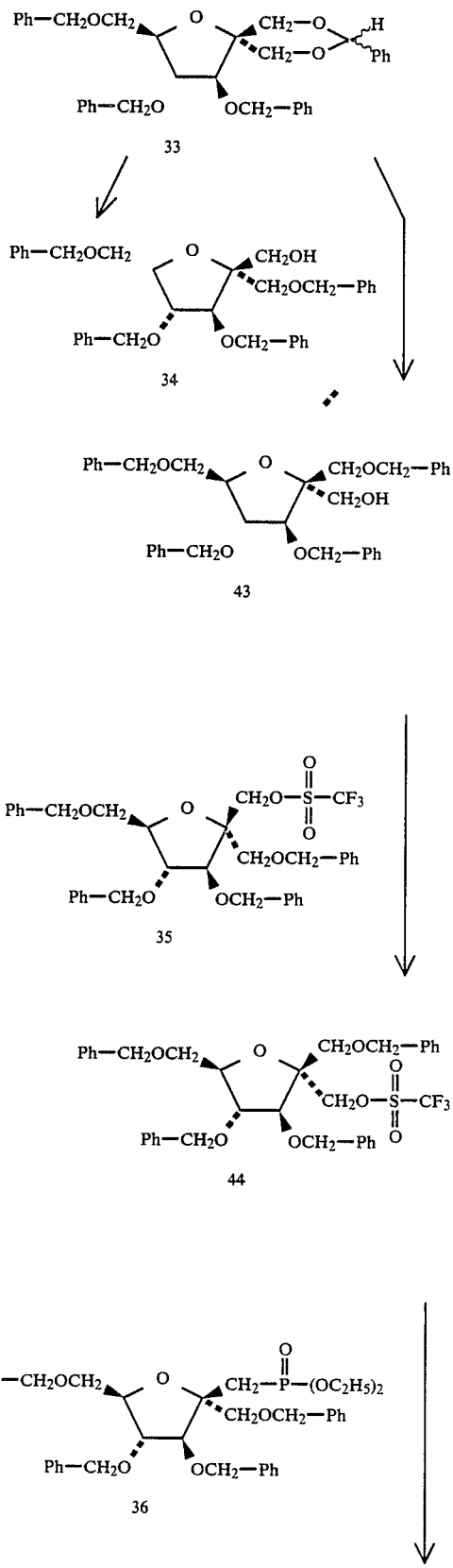

-continued
Flowchart D
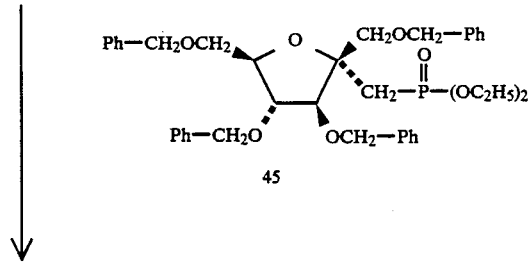
45
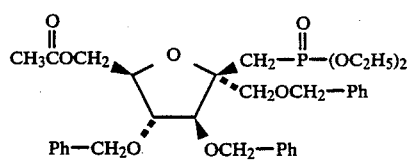
37
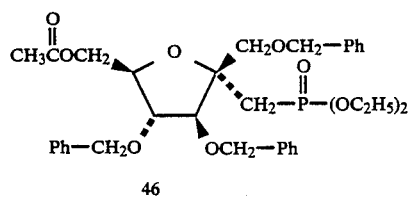
46
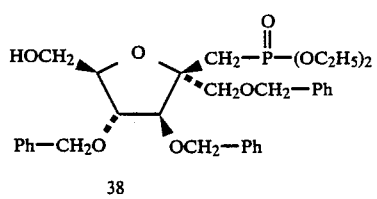
38
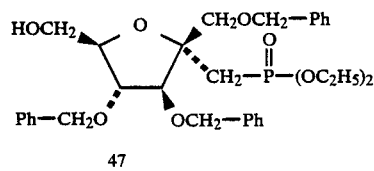
47
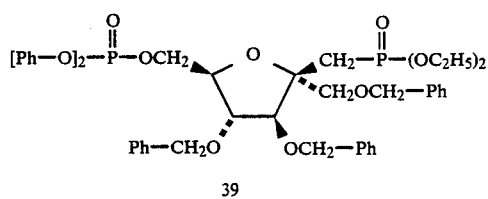
39
-continued
Flowchart D
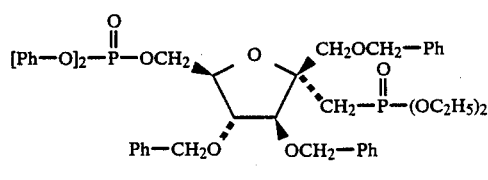
48
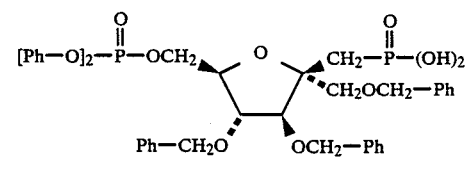
40
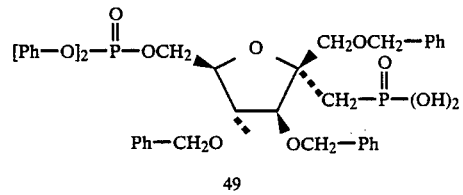
49
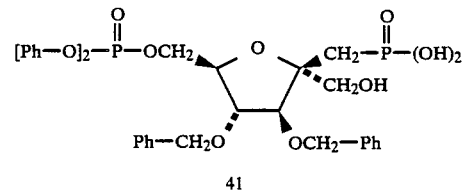
41
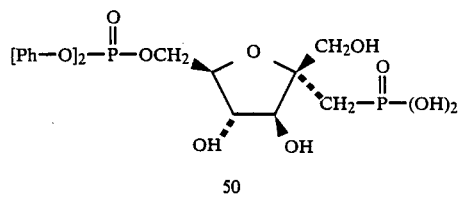
50

Flowchart D -continued

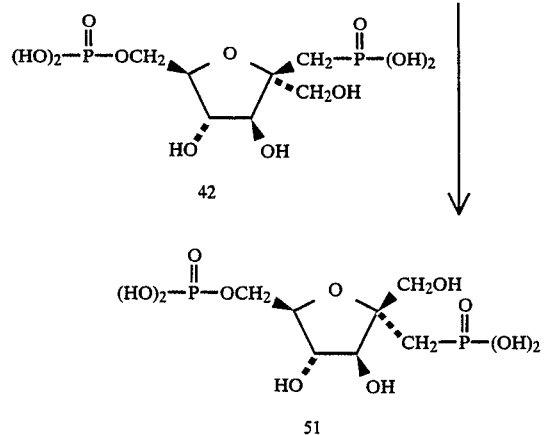

According to Flowchart D, 2,5-anhydro-3,4,6-tris-O-(phenylmethyl)-D-mannose 27 is reacted with formalin and potassium carbonate in methanol, giving 2,5-anhydro-2-C-(hydroxymethyl)-3,4,6-tris-O-(phenylmethyl-D-glucitol 32, which is then reacted with benzaldehyde dimethyl acetal and p-toluene sulfonic acid in dimethylformamide giving 2,5-anhydro-2-C-(hydroxymethyl)-3,4,6-tris-O-(phenylmethyl)-1,2$^1$-O-(phenylmethylene)-[R (and S)]-glucitol, 33. The epimeric mixture, 33, is reacted with lithium aluminum hydride and aluminum chloride in dichloromethane:ether (1:1), giving 2,5-anhydro-2-C-[(phenylmethoxy)methyl]-3,4,6-tris-O-(phenylmethyl)-D-glucitol, 34, and its D-mannitol epimer 43 which were separated by silica gel chromatography. Compound 34 is reacted with triflic anhydride in pyridine-dichloromethane, giving 2,5-anhydro-2-C-[(phenylmethoxy)methyl]-3,4,6-tris-O-(phenylmethyl)-D-glucitol, 1-(trifluoromethanesulfonate), 35. Compound 35 is reacted with sodium diethylphosphite in tetrahydrofuran, giving 2,5-anhydro-1-deoxy-1-(diethoxyphosphinyl)-2-C-[(phenylmethoxy)methyl]-3,4,6-tris-O-(phenylmethyl)-D-glucitol, 36, which is reacted with acetic anhydride and boron trifluoride etherate under an inert atmosphere in an ice bath, giving 2,5-anhydro-1-deoxy-1-(diethoxyphos-phinyl-2-C-[(phenylmethoxy)methyl]-3,4-bis-O-(phenylmethyl)-D-glucitol, 6-(acetate), 37. Compound 37 is reacted with sodium ethoxide in ethanol, giving 2,5-anhydro- 1-deoxy-1-(diethoxyphosphinyl)-2-C-[(phenylmethoxy)-methyl]-3,4-bis-0-(phenylmethyl)-D-glucitol 38 which is treated with diphenyl chlorophosphate in pyridine in an ice bath, giving 2,5-anhydro-1-deoxy-1-(diethoxyphosphinyl)-2-C-[(phenylmethoxy)methyl]-3,4- bis-0-(phenylmethyl)-D-glucitol, 6-(diphenyl phosphate), 39. Compound 39 is treated with trimethylsilyl bromide in dichloromethane under an inert atmosphere, giving, 2,5-anhydro-1-deoxy-2-C-[(phenylmethoxy)methyl]-3,4-bis-O-(phenylmethyl)-1-phosphono-D-glucitol, 6-(diphenyl phosphate), 40 which is sequentially hydrogenated giving 2,5-anhydro-1-deoxy-2-C-(hydroxymethyl)-1-phosphono-D-glucitol, 6-(diphenyl phosphate), 41, and then the desired product 2,5-anhydro-l-deoxy-2-C-(hydroxymethyl)-1-phosphono-D-glucitol, 6-(dihydrogen phosphate) 42.

Epimer 43 is converted (through D-mannitol derivatives 44, 45, 46, 47, 48, 49 and 50) to the product 2,5-anhydro-1-deoxy-2-C-(hydroxymethyl)-1-phosphono-D-mannitol, 6-(dihydrogen phosphate) 51, according to procedures described above.

Compounds 42 and 51 are disclosed in R. Meuwly and A. Vasella, *Helvetica Chim. Acta.* 69, 751-760 (1986), but are prepared by a different process.

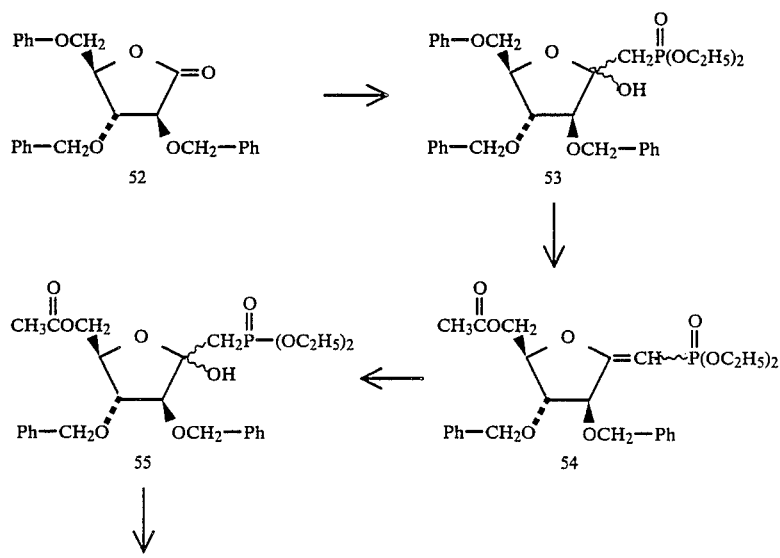

Flowchart E

Flowchart E

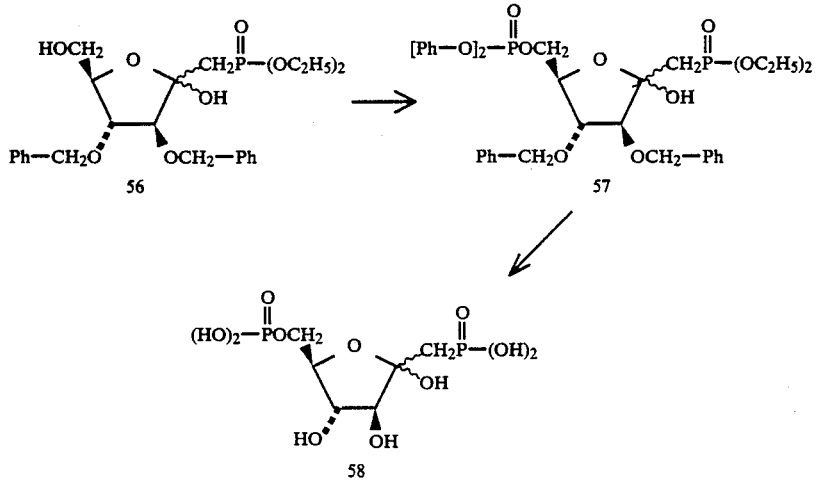

In accordance with Flowchart E, treatment of 2,3,5-tris-O-(phenylmethyl)-D-arabinonic acid, gammalactone 52 with lithio diethyl methylphosphonate provides the furanose 53. Treatment of 53 with boron trifluoride etherate in acetic anhydride gives the D-arabino-hex-1-enitol-6-monoacetate 54 as a mixture of Z and E isomers. Hydration of 54 with trifluoroacetic acid in wet dichloromethane provides the furanose 55 which is deacetylated with ethanolic sodium ethoxide giving the diol 56. Treatment of 56 with diphenyl chorophosphate provides the phosphate triester 57 which is deprotected by successive reaction with trimethylsilyl bromide in dichloromethane, hydrogenolysis in the presence of palladium hydroxide and hydrogenolysis in the presence of platinum, giving 1-deoxy-1-phosphono-D-fructofuranose, 6-(dihydrogen phosphate) 58

Other esters of the formulae:

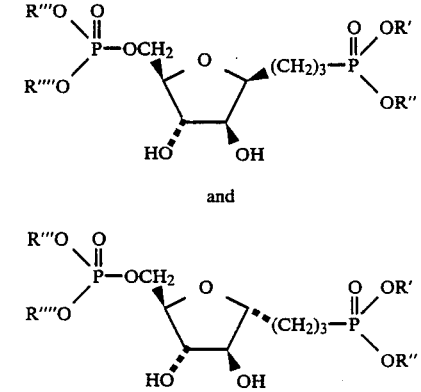

may be prepared by any of the following methods A, B, C or D.

Method A

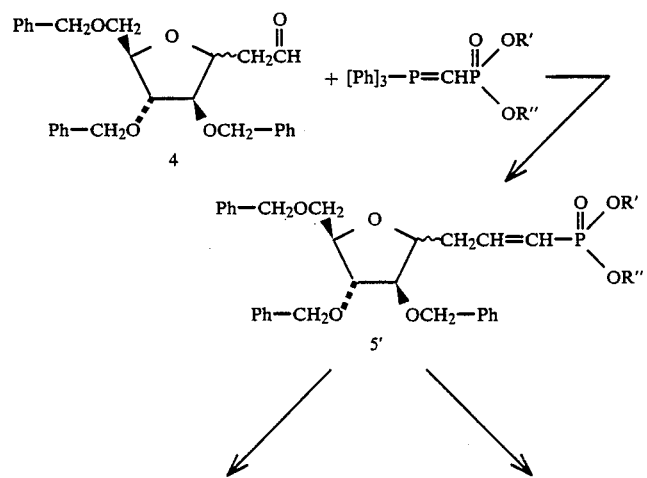

Method A

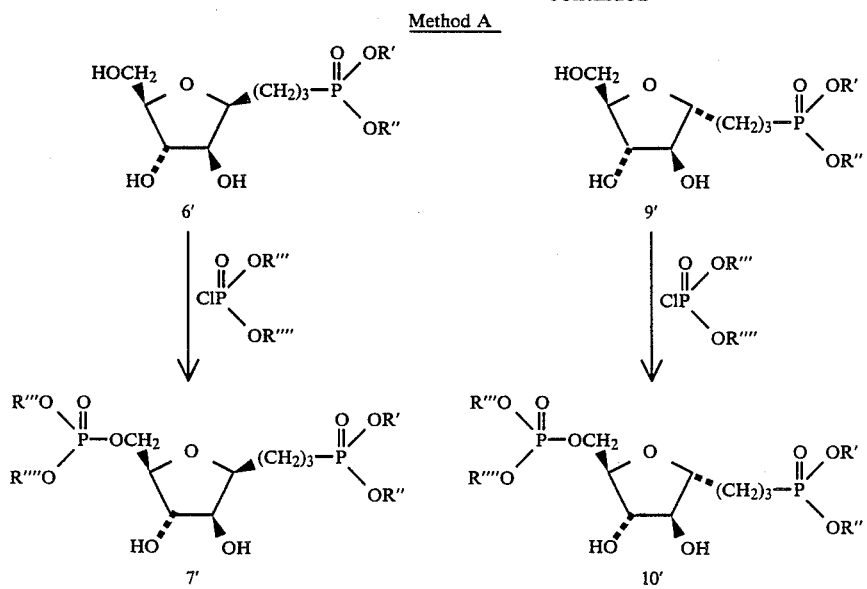

In Method A, 3,6-anhydro-2-deoxy-4,5,7-tris-O-(phenylmethyl)-D-gluco (and D-manno) heptose mixture 4 is reacted with a disubstituted triphenylphosphoranylidenemethyl phosphonate where R' and R" may be any of the aromatic substituents listed in Table I, giving the isomeric mixture 4,7-anhydro-1,2,3-trideoxy-1-(disubstituted phosphinyl)-5,6,8-tris-O-(phenylmethyl)-D-gluco (and D-manno)-oct-1-enitol, 5', which is hydrogenated in methanol and glacial acetic acid over palladium on carbon, and then subjected to chromatography, giving the separate isomers 4,7-anhydro-1,2,3-trideoxy-1-(disubstituted phosphinyl)-D-glucooctitol, 6', and 4,7-anhydro-1,2,3-trideoxy-1-(disubstituted phosphinyl)-D-manno-octitol 9'. The isomers 6' and 9 are individually reacted with a disubstituted chlorophosphate where R''' and R'''' may be selected independently of one another from any of the substituents listed in Table IV, giving 4,7-anhydro-1,2,3-trideoxy-1-(disubstituted phosphinyl)-D-oluco-heptitol, 8-(disubstituted phosphate) 7' and the corresponding D-manno derivative 10'.

Method B

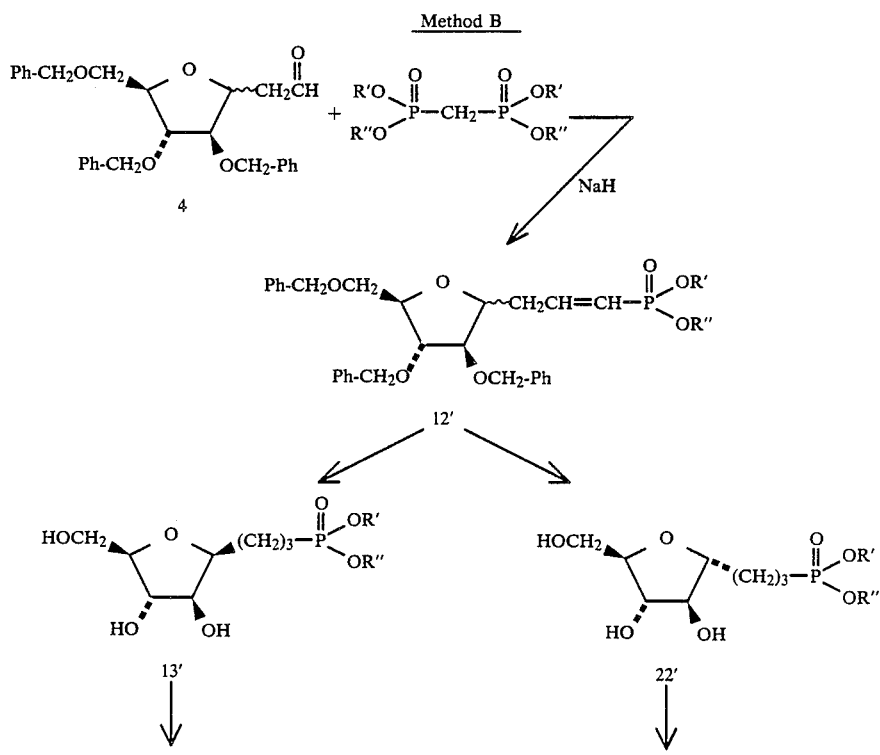

-continued

Method B

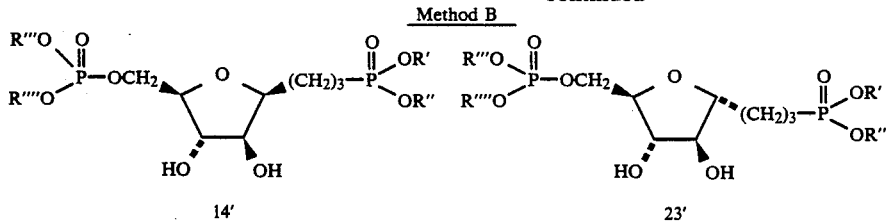

In Method B, 3,6-anhydro-2-deoxy-4,5,7-tris-O-(phenylmethyl)-D-gluco (and D-manno) heptose mixture 4 is reacted with a tetrasubstituted bisphosphonate, where and R' and R" may be any of the aliphatic substituents listed in Table II, and sodium hydride in dimethoxy ethane, giving the isomeric mixture 2,5-anhydro-1-deoxy-1-C-(disubstituted phosphinyl)-3,4,6-tris-O-(phenylmethyl)-D-glucitol and D-mannitol 12' which are then reacted as described in Method A giving 2,5-anhydro-1-deoxy 1-(disubstituted phosphinyl)-D-mannitol, 6-(disubstituted phosphate) 14' and the corresponding D-glucitol derivative 23'.

dium hydride and a disubstituted phosphite where R' and R" may be any of the aliphatic or aromatic substituents listed in Table III giving the phosphite derivatives which are separated and then reacted as described in Method A, giving the disubstituted phosphates 8' and 11".

Method D

In Method D, the free acid forms of the novel compounds of this invention (R', R", R''', R'''' are all hydrogen), can be alkylated using a suitable diazo reagent, such as those described in Table V below, in anhydrous

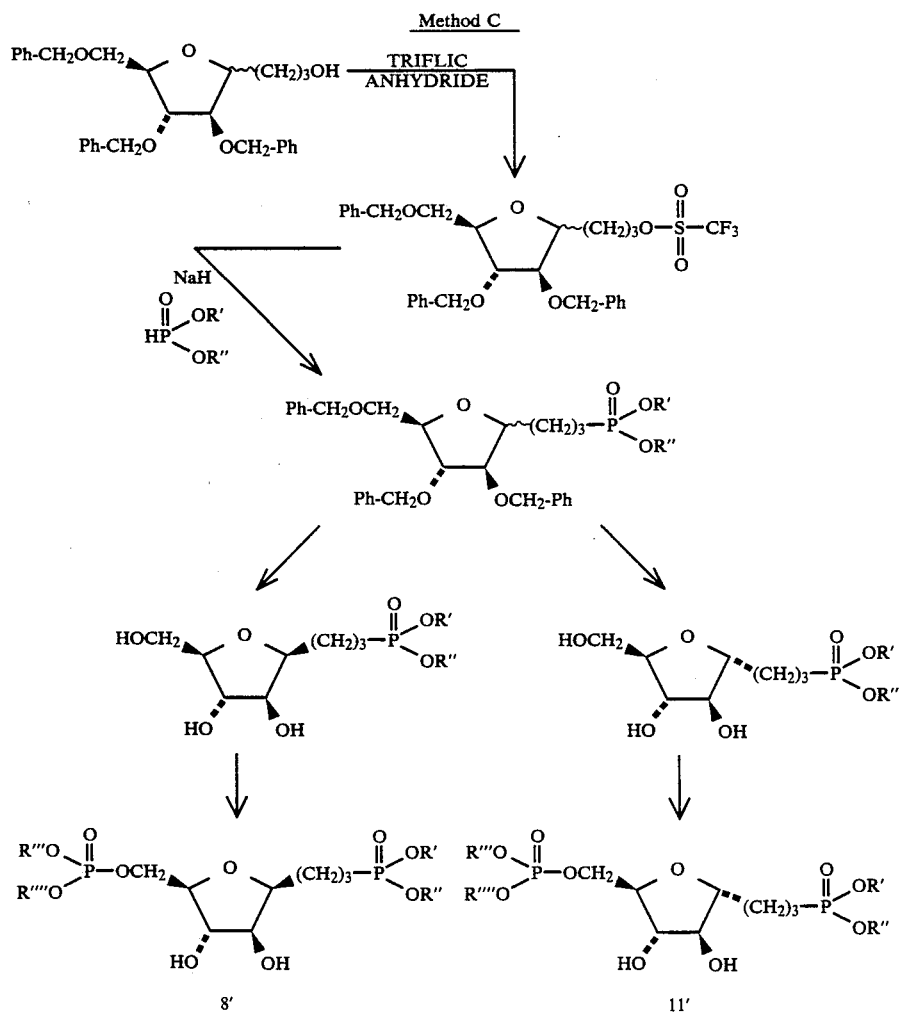

In Method C, the mixture 4,7-anhydro-2,3-di-deoxy-5,6,8-tris-O-(phenylmethyl)-D-gluco-octitol and 2,5-anhydro-6,7-dideoxy-1,3,4-tris-O-(phenylmethyl)-D-manno-octitol is reacted with triflic anhydride to produce the triflate shown which is then reacted with somethanol at 0°–5° C., followed by the addition of acetic acid, evaporation and purification by chromatography, giving tetraesters where each of the ester substituents are the same in the resulting tetraesters.

Other esters of the formulae:

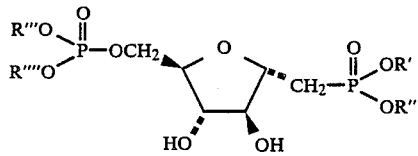

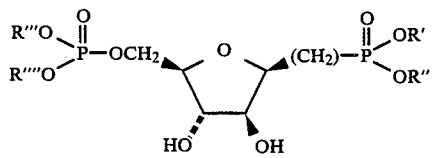

may be prepared by the above described Method B from 2,3,5-tris-O-(phenylmethyl)-D- arabinofuranose or by Method C from 2,5-anhydro-1,3,4-tris-O-(phenylmethyl)-D-mannitol-D-glucitol mixture, giving the compounds:

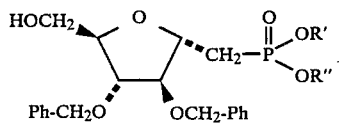

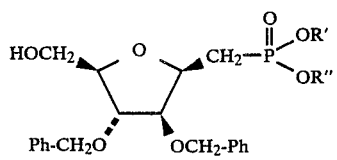

which are then phosphorylated with any of the reagents listed in Table IV followed by debenzylation.

These compounds may also be prepared by reacting the dihydrogen phosphate derivatives with diazo reagents as described in Method D.

Esters of the formula:

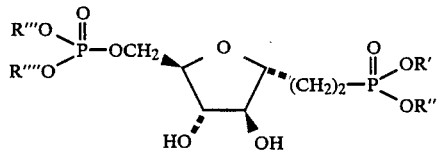

may be prepared as described in Method A from 2,5-anhydro-3,4,6-tris-O-(phenylmethyl)-D-mannose or both isomers may be prepared as described in Method C from 3,6-anhydro-2-deoxy-4,5,7-tris-O-(phenylmethyl)-D-gluco-hepitol and 2,5-anhydro-6-deoxy-1,3,4-tris-O-(phenylmethyl)-D-manno-hepitol mixture giving

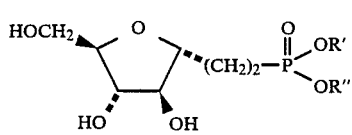

-continued

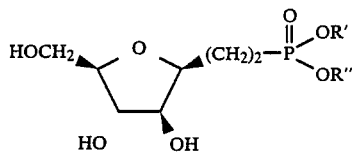

which can be separated and then phosphorylated with a dialkyl or diaryl chlorophosphate selected from those of Table IV. Alternately, these compounds may be prepared by reacting the dihydrogen phosphate derivatives with a diazo reagent as described in Method D.

Esters of the formulae:

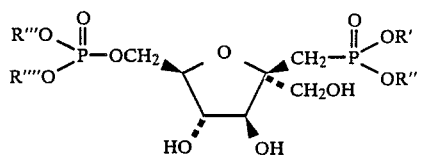

may be prepared by the above described Method C from 2,5-anhydro-2-[(phenylmethoxy)methyl]-3,4,6-tris-O-(phenylmethyl)-D-glucitol (or D-mannitol), 1-(trifluoromethanesulfonate) giving the compounds:

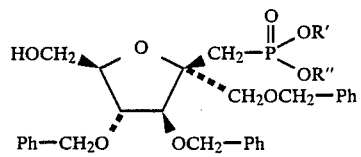

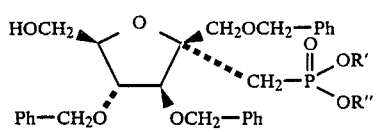

which are then phosphorylated using the reagents of Table IV and then debenzylated. Alternatively, the dihydrogen phosphate derivatives (R'=R''=H) may be reacted with the diazo reagents as described in Method D.

TABLE I $$(Ph)_3-P=CHP\begin{matrix}O\\||\end{matrix}\begin{matrix}OR'\\OR''\end{matrix}$$

| R', R'' | Reference |
|---|---|
| (phenyl) | (1) G. H. Jones, et al., Tetrahedron Letters, 573 (1968). |

TABLE I-continued $$(Ph)_3-P=CHP\overset{O}{\underset{OR''}{\parallel}}\!\!\!\begin{array}{c}OR'\\OR''\end{array}$$

| R', R'' | Reference |
|---|---|
| 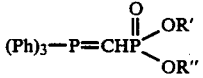 (o-tolyl, CH₃) | (2) K. Sasse, in: Houben-Weyl, Methoden der Organischen Chemie, 4th Edition, Vol XII/2, E. Miller, Ed., Georg Thieme Verlag, Stuttgart (1964). |
| 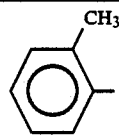 (2,4,6-trimethylphenyl) | |
| 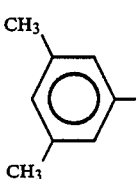 (y-phenyl)<br>(y = alkoxy, alkyl, halo) | |

TABLE II $$R'O\underset{R''O}{\overset{O}{\parallel}}\!\!P-CH_2-P\underset{OR''}{\overset{O}{\parallel}}\!\!\!\begin{array}{c}OR'\\OR''\end{array}$$

| R', R'' | Reference |
|---|---|
| CH₃— | (2) Vide supra |
| C₂H₅— | (3) J. A. Cade, J. Chem. Soc. 2266(1959) |
| (CH₃)₂CH— (or any C₃-C₈ n-alkyl or iso-alkyl, or C₃-C₆ cycloalkyl) | (4) C. H. Roy U.S. Pat. No. 3,251,907 |
| R' + R'' = —CH₂CH₂CH₂— | |

TABLE III $$HP\overset{O}{\underset{OR''}{\parallel}}\!\!\!\begin{array}{c}OR'\\OR''\end{array}$$

| R', R'' | References |
|---|---|
| 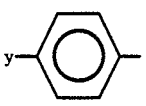 (phenyl) | (2) Vide supra, or commercially available |
| 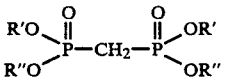 (y-phenyl)<br>(y = alkoxy, alkyl, halo) | |
| C₂H₅— | |
| CH₃— | |
| n-alkyl or iso alkyl (C₃-C₈) or C₃-C₆ cycloalkyl | |
| ZCH₂CH₂ (Z = CH₂S, halo) | |

TABLE IV $$R'''O\underset{R''''O}{\overset{O}{\parallel}}\!\!P-Cl$$

R''', R''''

Straight or branched chain alkyl (C₁-C₁₈)
Cl₃CCH₂—
CH₂=CHCH₂—
phenyl
mono- and di-substituted phenyl [substituents = straight or branched chain alkyl (C₁-C₆), alkoxy (C₁-C₆), NO₂, halogen]
phenylmethyl, substitued phenylmethyl
substituents = NO₂, alkoxy (C₁-C₆), straight or branched chain alkyl (C₁-C₁₈)
halogen] ZCH₂CH₂—[Z = SO₂R₂, SR₂, OR₂, Si(R₂)₃ (R₂ = alkyl (C₁-C₃))]

| | |
|---|---|
|  | [R₃ = alkyl (C₁-C₃), R₃—R₃ = alkylene, acetal] |
| (benzyl CH₂—) | |
| R₄ isopropyl-like | [R₄ = H, CH₃] |
| R₅ / R₆ | [R₅ = H, R₆ = F, OH, OR₇<br>[R₇ = alkyl (C₁-C₆), acryl, cycloalkyl] or when R₅ = R₆ they are hydrogen, fluoro or alkyl (C₁-C₄)]] |
| 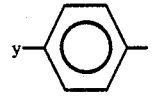 (OR₈) | [R₈ = hydrogen, alkyl (C₁-C₁₈), aryl] |

These reagents are commercially available or are synthesized according to L. A. Slotin, Synthesis, 737 (1977); K. Sasse in Houben-Weyl, Methoden der Organischen Chemie, 4th Edition, Vol. XII/2, E. Miller Ed., Georg Thieme Verlag, Stuttgart (1964); R. N. Houston et al., J. Med. Chem., 27, 440 (1984); P. Halvary and J. Weller, Helv. Chim. Acta., 69, 1862 (1986).

Reagents for mixed esters (R' not equal to R'' or R''' not equal to R'''') may be synthesized using the same methods.

TABLE V

| Diazo Reagent* |
|---|
| CH₂N₂ |
| Ph-CHN₂ |
| CH₃CHN₂ |
| (CH₃)₂ CN₂ |

*Reagents are freshly prepared according to K. Sasse (vide supra); K. Bruzik and M.-D. Tsai, J. Am. Chem. Soc. 106, 747 (1984); Fieser and Fieser, Reagents for Organic Synthesis, Volumes 1 and 2, Wiley Interscience.

The novel compounds of this invention were tested for their ability to stimulate the enzyme 6-phosphofructo-1-kinase ("PFK") and for their ability to inhibit the enzyme fructose-1,6-bisphosphatase ("FBP") using the procedures described below.

Effects on the activity of PFK were determined using an aldolase-coupled, spectrophotometric assay. The assay mixture contained: 50 nM N-tris-(hydroxymethyl)-methyl-2-aminoethanesulfonic acid, hydrochloride ("TES-HCl", pH 7.3); 1 mM ethylenediaminetetraacetic acid ("EDTA"); 6 mM magnesium chloride; 2.5 mM dithiothreitol; 0.165 mM nicotinamide adenine dinucleotide ("NADH"); 1 mM adenosine triphosphate ("ATP"); 0.04 U aldolase; 0.4 U triose phosphate isomerase; alpha-glycerolphosphate dehydrogenase (1.5 U/ml); 0.1 U of purified rat liver 6-phosphofructo-1-kinase; and various concentrations of the test compound, all in a final volume of 1 ml. The mixture was preincubated for 3 minutes at 30° C. and then the reaction was initiated with 0.2 mM fructose-6-phosphate. The rate of decrease in absorbance at 340 nM was measured at 30° C. with a recording spectrophotometer.

Effects on the activity of FBP were determined using a spectrophotometric assay. The assay mixture contained 100 mM tris(hydroxymethyl)aminomethane, hydrochloride ("TRIS-HCl", pH 7.4); 2.5 mM betamercaptoethanol; 2 mM magnesium chloride; 0.05 mM EDTA; 0.2 mM nicotinamide adenine dinucleotide phosphate ("NADP"); 10 U phosphoglucose isomerase; 5 U glucose-6-phosphate dehydrogenase; 0.02 U of purified rat liver FBP; and various concentrations of the test compound, all in a final volume of 1 ml. The mixture was preincubated for 3 minutes at 30° C. and then the reaction was initiated with 0.02 mM fructose-1,6-bisphosphate. The rate of increase in absorbance at 340 nM was measured at 30° C. with a recording spectrophotometer.

The results of these tests on representative compounds of this invention are shown in Table VI.

TABLE VI

| Compound | PFK ED$_{50}$($\mu$M) | FBP IC$_{50}$($\mu$M) |
| --- | --- | --- |
| Beta-D-Fructose-2,6-bisphosphate (control) | 0.02 | 3 |
| 4,7-Anhydro-1,2,3-trideoxy-1-(dihydroxyphosphinyl)-D-gluco-octitol, 8-(dihydrogen phosphate) | 12 | — |
| 4,7-Anhydro-1,2,3-trideoxy-1-(dihydroxyphosphinyl)-D-manno-octitol, 8-(dihydrogen phosphate) | 27 | 200 |
| 3,6-Anhydro-1,2-dideoxy-1-phosphono-D-manno-heptitol, 7-(dihydrogen phosphate) | 6 | 80 |
| 2,5-Anhydro-1-deoxy-1-phosphono-D-glucitol, 6-(dihydrogen phosphate) | 20 | 602 |
| 2,5-Anhydro-1-deoxy-1-phosphono-D-mannitol, 6-(dihydrogen phosphate) | 4 | 58 |
| 2,5-Anhydro-1-deoxy-2-C-(hydroxymethyl)-1-phosphono-D-glucitol, 6-(dihydrogen phosphate) | 12 | 240 |
| 2,5-Anhydro-1-deoxy-2-C-(hydroxymethyl)-1-phosphono-D-mannitol, 6-(dihydrogen phosphate) | 6 | 393 |

Although the naturally-occurring control compound had more in vitro activity, the compounds of this invention are more stable, so that they will provide more efficacious control over the glycolytic and gluconeogenic processes in mammals.

The compounds of Formulae I and II are normally administered to mammals in the form of their tetraesters, that is, where R',R",R''' and R'''' are C$_1$ to C$_6$ alkyl, C$_3$ to C$_6$ cycloalkyl or phenyl. The esters, being more lipophilic than the acids (R', R", R''' and R''''=H), pass through the mammalian cell wall more readily.

When the compounds of the present invention are employed for the above described utility, they may be combined with one or more pharmaceutically acceptable carriers, for example, solvents, diluents and the like, and may be administered in such forms as tablets, capsules, dispersible powders, granules or suspensions containing, for example, from about 0.5 to 5.0% of suspending agent, syrups containing, for example, from about 10 to 50% of a carrier, and elixirs containing, for example, from about 20 to 50% of ethanol, and the like, or parenterally in the form of sterile injectable solutions or suspensions containing from about 0.5 to 5.0% suspending agent in isotonic medium. These pharmaceutical preparations may contain for example, from about 0.5 to 90.0% of the active ingredient in combination with the carrier, more usually between 5.0 and 60.0% by weight.

The effective dosage of active ingredient employed may vary depending on the particular compound, the mode of administration and the severity of the conditions being treated. However, in general, satisfactory results are obtained when the compounds of this invention are administered at a daily dosage of from about 1 mg to about 50 mg per kg of body weight, preferably given in divided doses two to four times daily or in sustained release form. Dosage forms suitable for internal use comprise from about 1 mg to about 50 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. The compounds may be administered by a variety of routes including oral, intravenous, intramuscular and subcutaneous. Solid carriers include starch, lactose, dicalcium phosphate, microcrystalline cellulose, and kaolin; while liquid carriers include sterile water, polyethylene glycols, non-ionic surfactants and edible oils such as corn, peanut and sesame oils, as appropriate to the nature of the active ingredient and the particular form of administration desired. Adjuvants customarily employed in the preparation of pharmaceutical compositions may be advantageously included, such as flavoring agents, coloring agents, preservatives and antioxidants, e.g. vitamin E, ascorbic acid, butylated hydroxytoluene, and the like.

The preferred pharmaceutical compositions in terms of ease of preparation are solid compositions, particularly tablets and hard-filled or liquid-filled capsules. Oral administration of the compounds is preferred. These compounds may, however, be administered parenterally or intraperitoneally. Solutions or suspensions of the active compounds can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparations of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a polyol such as glycerol, propylene glycol or liquid polyethylene glycol, suitable mixtures thereof, or vegetable oils.

The invention will be more fully described in conjunction with the following specific examples which are not to be construed as limits thereon.

EXAMPLE 1

2,3-Dideoxy-4,5,7-tris-0-(phenylmethyl)-D-arabino-3-heptulo-3,6-furanosonic acid, ethyl ester A 2.0 g portion of sodium hydride (50% oil dispersion) was washed with hexane and dried. To this was added 40 ml of dried dimethoxyethane and 9.0 g of triethylphosphonoacetate in an ice bath. This reagent was stirred for 1 hour at room temperature.

An 8.4 g portion of 2,3,5-tris-O-(phenylmethyl)-D-arabinofuranose was added to the above reagent; the mixture was stirred for 1 day at room temperature, then poured into ice water and extracted with ether. The extract was dried and then evaporated to give 10.6 g of an oil. This oil was chromatographed on a silica gel column eluting with hexane:ethyl acetate (9:1), to yield 8.2 g of the desired product.

EXAMPLE 2

3,6-Anhydro-2-deoxy-4,5,7-tris-O-(phenylmethyl)-D-gluco-heptitol and
2,5-anhydro-6-deoxy-1,3,4-tris-O-(phenylmethyl)-D-manno-heptitol 2,3-Dideoxy-4,5,7-tris-0-(phenylmethyl)-D-arabino-3-heptulo-3,6-furanosonic acid, ethyl ester (4.9 g) was dissolved in 75 ml of dry ether and added dropwise to a slurry of 670 mg of lithium aluminum hydride in 50 ml of ether under an argon atmosphere. After 3 hours at room temperature this mixture was treated with 7 ml of saturated aqueous sodium sulfate solution. The solids were removed by filtration and washed with ether. The wash was combined with the filtrate, washed with brine, dried and evaporated to afford 4.47 g of product which was purified further on silica gel.

EXAMPLE 3

3,6-Anhydro-2-deoxy-4,5,7-tris-O-(phenylmethyl)-D-gluco (and D-manno)-heptose

A 2.61 g portion of chromium trioxide was added to a magnetically stirred solution of 4.32 ml of pyridine in 68 ml of dichloromethane under an argon atmosphere. This solution was stirred for 20 minutes at room temperature, then a solution of 1.98 g of 3,6-anhydro-2-deoxy-4,5,7-tris-O-(phenylmethyl)-D-gluco(and D-manno)-heptitol, in 4.5 ml of dichloromethane was added. After stirring for 25 minutes the solution was decanted from the black residue. The residue was washed with ether and the combined organic solution washed successively with three 45 ml portions of 5% aqueous sodium hydroxide, 45 ml of 5% aqueous hydrochloric acid, 45 ml of 5% aqueous sodium bicarbonate, and 45 ml of brine, and dried. The solvent was removed giving an oil which was chromatographed on silica gel, eluting with hexane:ethyl acetate (4:1) giving 1.46 g of the desired isomeric mixture.

EXAMPLE 4

4,7-Anhydro-1,2,3-trideoxy-1-(diphenoxyohosphinyl)-5,6,8-tris-O-(phenylmethyl)-D-gluco (and D-manno)-oct-1-enitol A mixture of 1.40 g of 3,6-anhydro-2-deoxy-4,5,7-tris-O-(phenylmethyl)-D-gluco(and D-manno)heptose and 1.74 g of diphenyl triphenylphosphoranylidenemethylphosphonate were dissolved in 8.5 ml of dry toluene. The resulting solution was heated at reflux temperature for 20 hours. The crude mixture was then chromatographed on silica gel, eluting with hexane:ethyl acetate (3.5:1), giving 1.40 g of the desired epimeric compounds as a mixture.

EXAMPLE 5

4,7-Anhydro-1,2,3-trideoxy-1-(diphenoxyohosphinyl)-D-gluco-octitol

A 1.27 g portion of a mixture of 4,7-anhydro-1,2,3-trideoxy-1-(diphenoxyphosphinyl)-5,6,8-tris-O-(phenylmethyl)-D-gluco-oct-1-enitol and the corresponding D-manno-oct-1-enitol was dissolved in a mixture of 30 ml of methanol and 20 ml of glacial acetic acid and hydrogenated at 60 psi pressure with 10% palladium on carbon catalyst for 18 hours. The mixture was then filtered and the solvent removed giving 940 mg of a yellow oil. This oil was flash chromatographed on silica gel, eluting with methanol in dichloromethane. A total of 270 mg of the pure gluco (less polar) and 240 mg of the pure manno-isomer (see Example 8) was obtained.

EXAMPLE 6

4,7-Anhydro-1,2,3-trideoxy-1-(diphenoxyphosphinyl)-D-gluco-octitol, 8-(diphenyl phosphate)

A 215 mg portion of 4,7-anhydro-1,2,3-trideoxy-1-(diphenoxyphosphinyl)-D-gluco-octitol was dissolved in 1.5 ml of pyridine and this solution cooled in an ice bath. A 213 mg portion of diphenyl chlorophosphate was added and the solution stored in a freezer overnight. The mixture was then treated with two drops of water, warmed to room temperature and concentrated in vacuo. The residue was taken up in dichloromethane, washed with water, cold 1N hydrochloric acid and saturated sodium bicarbonate, and the solution dried and evaporated. The resulting oil was purified by flash chromatography, to afford 232 mg of the desired compound.

EXAMPLE 7

4,7-Anhydro-1,2,3-trideoxy-1-(dihydroxyphosphinyl)-D-gluco-octitol, 8-(dihydrogen phosphate)

A 190 mg portion of 4,7-anhydro-1,2,3-trideoxy-1-(diphenoxyphosphinyl)-D-gluco-octitol, 8-(diphenyl phosphate) in 20 ml of methanol was deprotected by catalytic hydrogenation using platinum oxide in a Parr apparatus. When hydrogen uptake was complete, the mixture was filtered. The filtrate was evaporated in vacuo, giving 105 mg of the desired product as a colorless oil.

EXAMPLE 8

4,7-Anhydro-1,2,3-trideoxy-1-(diphenoxyphosphinyl)-D-manno-octitol

Combined latter fractions from Example 5 were evaporated giving 240 mg of the desired compound.

EXAMPLE 9

4,7-Anhydro-1,2,3-trideoxy-1-(diphenoxyohosphinyl)-D-manno-octitol, 8-(diphenyl phosphate) A 240 mg portion of 4,7-anhydro-1,2,3-trideoxy-1-(diphenoxyphosphinyl)-D-manno-octitol was reacted with 225 mg of diphenyl chlorophosphate in 1.7 ml of pyridine as described in Example 6, giving, after chromatography, 120 mg of the desired compound.

EXAMPLE 10

4,7-anhydro-1,2,3-trideoxy-1-(dihydroxyphosphinyl)-D-manno-octitol, 8-(dihydrogen phosphate)

A 120 mg portion of 4,7-anhydro-1,2,3-trideoxy-1-(diphenoxyphosphinyl)-D-manno-octitol, 8-(diphenyl phosphate) was hydrogenated as described in Example 7, giving 66 mg of the desired product as a colorless oil.

EXAMPLE 11

2,5-Anhydro-1-deoxy-1-(diethoxyphosphinyl)-3,4,6-tris-O-(phenylmethyl)-D-glucitol and D-mannitol mixture A 4.23 g portion of 2,3,5-tris-O-(phenylmethyl)-D-arabinofuranose was added to a freshly prepared solution of 5.76 g of tetraethylmethylenebisphosphonate and 480 mg of sodium hydride in 40 ml of freshly distilled dimethoxyethane after the solution had been stirred for one hour. The final mixture was stirred overnight under argon, then poured into ice water and extracted with ether. The extract was dried and evaporated to an oil which was purified by chromatography on silica gel, eluting with ethyl acetate:hexane:methanol (40:60:2) giving 4.16 g of the desired compounds as a mixture.

EXAMPLE 12

2,5-Anhydro-1-deoxy-1-(diethoxyphosphinyl)-3,4-bis-O-(phenylmethyl)-D-glucitol, and D-mannitol, 6-(acetate)

A 1.58 g portion of 2,5-anhydro-1-deoxy-1-(diethoxyphosphinyl)-3,4,6-tris-O-(phenylmethyl)-D-glucitol and D-mannitol mixture was placed in a flask under an argon atmosphere. A 9.3 ml portion of acetic anhydride was added and the mixture was stirred in an ice bath. A 370 µl portion of cold boron trifluoride etherate was syringed into the mixture After 40 minutes 100 µl of boron trifluoride etherate was added and stirring was continued at 0° C. for 35 minutes. A 1.6 ml portion of saturated aqueous sodium bicarbonate was added, the mixture was stirred at 0° C. for 20 minutes, then room temperature for 20 minutes and then evaporated. The residue was taken up in ether/water. The ether layer was washed with brine, dried, filtered and the solvent removed. The residual oil was purified by flash chromatography on silica gel giving 1.20 g of the desired compounds as a mixture.

EXAMPLE 13

2,5-Anhydro-1-deoxy-1-(diethoxyphosohinyl)-3,4-bis-O-(phenylmethyl)-D-mannitol

A 702 mg portion of 2,5-anhydro-1-deoxy-1-(diethoxyphosphinyl)-3,4-bis-O-(phenylmethyl)-D-mannitol, D-glucitol, 6-(acetate) mixture was dissolved in 3.2 ml of ethanol and treated with 290 µl of a freshly prepared 2.4N ethanolic solution of sodium ethoxide. After 1.5 hours the reaction was quenched with glacial acetic acid, the ethanol removed, the residue taken up in ether, washed with saturated sodium bicarbonate and brine, dried and evaporated, giving an oil. This oil was flash chromatographed eluting with a gradient of ethyl acetate:hexane.

Fractions containing the more polar isomer were combined giving 360 mg of the desired compound, as a solid, mp 91°–92 ° C.

Earlier fractions were used in Example 18.

EXAMPLE 14

2,5-Anhydro-1-deoxy-1-(diethoxyphosphinyl)-3,4-bis-O-(phenylmethyl)-D-mannitol, 6-(diphenyl phosphate)

A mixture of 520 mg of 2,5-anhydro-1-deoxy-1-(diethoxyphosphinyl)-3,4-bis-O-(phenylmethyl)-D-mannitol, 3 ml of pyridine and 470 µl of diphenyl chlorophosphate were reacted as described in Example 6, giving 770 mg of the desired compound after purification by chromatography.

EXAMPLE 15

2,5-Anhydro-1-deoxy-3,4-bis-O-(phenylmethyl)-1-phosphono-D-mannitol, 6-(diphenyl phosphate)

A 677 mg portion of 2,5-anhydro-1-deoxy-1-(diethoxyphosphinyl)-3,4-bis-O-(phenylmethyl)-D-mannitol, diphenyl phosphate was dissolved in 2.7 ml of dichloromethane and the solution degassed with argon. A 385 µl portion of trimethylsilyl bromide was syringed into the mixture which was then stirred for 2.5 hours at room temperature, followed by 1 hour at 35° C. The volatile components were removed in vacuo, 50 µl of water and 3 ml acetone were added and the solvent evaporated, giving 649 mg of the desired compound.

EXAMPLE 16

2,5-Anhydro-1-deoxy-1-phosphono-D-mannitol, 6-(diphenyl phosphate)

A 630 mg portion of 2,5-anhydro-1-deoxy-3,4-bis-O-(phenylmethyl)-1-phosphono-D-mannitol, 6-(diphenyl phosphate) was dissolved in 23 ml of methanol and hydrogenated over palladium on carbon catalyst at 60 psi pressure When hydrogen uptake was complete the mixture was filtered and the filtrate evaporated. The resulting oil was crystallized from chloroform, giving 240 mg of the desired compound, mp 134°–136° C.

EXAMPLE 17

2,5-Anhydro-1-deoxy-1-phosphono-D-mannitol, 6-(dihydrogen phosphate)

A 310 mg portion of 2,5-anhydro-1-deoxy-1-phosphono-D-mannitol, 6-(diphenyl phosphate) was hydrogenated with platinum oxide as described in Example 7, giving 195 mg of the desired product as an oil.

EXAMPLE 18

2,5-Anhydro-1-deoxy-1-(diethoxyphosphinyl)-3,4-bis-O-(phenylmethyl)-D-glucitol

Fractions containing the less polar isomer from Example 13 were combined giving 280 mg of the desired compound as an oil.

EXAMPLE 19

2,5-Anhydro-1-deoxy-1-(diethoxyphosphinyl)-3,4-bis-O-(phenylmethyl)-D-glucitol, 6-(diphenyl phosphate)

A 530 mg portion of 2,5-anhydro-1-deoxy-1-(diethoxyphosphinyl)-3,4-bis-O-(phenylmethyl)-D-glucitol was reacted as described in Example 14, giving 450 mg of the desired compound.

EXAMPLE 20

2,5-Anhydro-1-deoxy-3,4-bis-O-(phenylmethyl)-1-phosphono-D-glucitol, 6-(diphenyl phosphate) A 588 mg portion of 2,5-anhydro-1-deoxy-1-(diethoxyphosphinyl)-3,4-bis-O-(phenylmethyl)-D-glucitol, 6-(diphenyl phosphate) was reacted as described in Example 15, giving 590 mg of the desired compound.

EXAMPLE 21

2,5-Anhydro-1-deoxy-1-phosphono-D-glucitol, 6-(diphenyl phosphate)

A 570 mg portion of 2,5-anhydro-1-deoxy-3,4-bis-O-(phenylmethyl)-1-phosphono-D-glucitol, diphenyl phosphate was reduced with palladium on carbon as described in Example 16, giving 385 mg of the desired compound as an oil.

EXAMPLE 22

2,5-Anhydro-1-deoxy-1-phosphono-D-glucitol, 6-(dihydrogen phosphate)

A 370 mg portion of 2,5-anhydro-1-deoxy-1-phosphono-D-glucitol, 6-(diphenyl phosphate) was hydrogenated as described in Example 7, giving 220 mg of the desired product as an oil.

EXAMPLE 23

2,5-Anhydro-D-mannose

The title compound was made (0.10 mol scale) by the procedure of D. A. Otero and R. Simpson, *Carbohydr. Res.*, 128, 79–86 (1984) and used as a crude compound in Example 24.

EXAMPLE 24

2,5-Anhydro-D-mannose, dimethyl acetal

The 2,5-anhydro-D-mannose prepared in Example 23 was dissolved in 400 ml of anhydrous methanol and treated with 18 ml of acetyl chloride. The solution was heated at reflux for 3 hours, then neutralized with lead carbonate, filtered and the filtrate concentrated. The resulting oil was purified by chromatography, giving 14.9 g of the desired compound.

EXAMPLE 25

2,5-Anhydro-3,4,6-tris-O-(phenylmethyl)-D-mannose, dimethyl acetal

A 3.14 g portion of 2,5-anhydro-D-mannose, dimethyl acetal was dissolved in 120 ml of dry dimethylformamide and treated with 2.46 g of sodium hydride. The suspension was stirred for 1 hour, then 16.6 ml of benzyl bromide was added and the mixture was stirred overnight. After 18 hours 1.0 ml of benzyl bromide was added and stirring continued overnight, providing 6.0 g of the desired compound after chromatography.

EXAMPLE 26

2,5-Anhydro-3,4,6-tris-O-(phenylmethyl)-D-mannose

A 790 mg portion of 2,5-anhydro-3,4,6-tris-O-(phenylmethyl)-D-mannose, dimethyl acetal was dissolved in 25 ml of acetonitrile and treated with 3.3 ml of 48% aqueous tetrafluoroboric acid. After 20 minutes the reaction was quenched with solid sodium bicarbonate. The solvent was removed and the residue extracted with ether, giving 730 mg of a yellow oil. This oil was flash chromatographed, eluting with hexane:ethyl acetate, giving 530 mg of the desired compound.

EXAMPLE 27

3,6-Anhydro-1,2-dideoxy-1-(diphenoxyphosphinyl)-4,5,7-tris-O-(phenylmethyl)-D-manno-hept-1-enitol An 880 mg portion of 2,5-anhydro-3,4,6-tris-O-(phenylmethyl)-D-mannose was dissolved in 6 ml of dry toluene and treated with 1.11 g of diphenyl triphenylphosphoranylidenemethylphosphonate at reflux temperature for 36 hours. Purification by chromatography, eluting with hexane:ethyl acetate afforded 660 mg of the desired compound.

EXAMPLE 28

3,6-Anhydro-1,2-dideoxy-1-(diphenoxyohosphinyl)-D-manno-heptitol

A 610 mg portion of 3,6-anhydro-1,2-dideoxy-1-(diphenoxyphosphinyl)-4,5,7-tris-O-(phenylmethyl)-D-manno-hept-1-enitol in 18 ml of methanol was hydrogenated as described in Example 5, giving 290 mg of the desired compound after chromatography.

EXAMPLE 29

3.6-Anhydro-1,2-dideoxy-1-(diphenoxyphosphinyl)-D-manno-heptitol, 7-(diphenyl phosphate)

A 270 mg portion of 3,6-anhydro-1,2-dideoxy-1-(diphenoxyphosphinyl)-D-manno-heptitol was dissolved in 2 ml of pyridine, the solution cooled to 0° C. and treated with 212 $\mu$l of diphenyl chlorophosphate as described in Example 6, giving 145 mg of the desired compound.

EXAMPLE 30

3,6-Anhydro-1,2-dideoxy-1-phosphono-D-manno-heptitol, 7-(dihydrogen phosphate)

A 130 mg portion of 3,6-anhydro-1,2-dideoxy-1-(diphenoxyphosphinyl)-D-manno-heptitol, 7-(diphenyl phosphate) was hydrogenated as described in Example 7, giving 84 mg of the desired product as an oil.

EXAMPLE 31

2,5-Anhydro-2-C-(hydroxymethyl)-3,4,6-tris-O-(phenymethyl)-D-glucitol

A 1.18 g portion of 2,5-anhydro-3,4,6-tris-O-(phenylmethyl)-D-mannose was dissolved in 8.5 ml of methanol, treated with 5.11 ml of 37% formalin and 480 mg of potassium carbonate and the mixture immersed in an 85° C. bath. After 4 hours the mixture was cooled, neutralized with 3.5 ml of 10% sulfuric acid and the volatiles removed. The residue was extracted with chloroform, giving 0.86 g of the desired compound after chromatography.

EXAMPLE 32

2,5-Anhydro-2-C-(hydroxymethyl)-3,4,6-tris-O-(phenylmethyl)-1,2$^1$-O-(phenylmethylene)-[R(and S)]-glucitol A 1.40 g portion of 2,5-anhydro-2-C-(hydroxymethyl)-3,4,6-tris-O-(phenylmethyl)-D-glucitol, 568 μl of benzaldehyde dimethyl acetal, 2.1 ml of dry dimethylformamide and 10 mg of p-toluenesulfonic acid were placed in a 15 ml flask attached to a rotary evaporator. After rotating under aspirator pressure in a 60° C. bath for 1 hour, 0.5 ml of dimethylformamide and 50 μl of benzaldehyde dimethyl acetal were added. Stirring was continued at 60° C. for 30 minutes, then at 65° C. for 30 minutes followed by evaporation of the solvent at 90° C. The residue was dissolved in chloroform and saturated aqueous sodium bicarbonate. The aqueous layer was washed with chloroform and the combined organic solution dried and evaporated giving 2 g of a yellow oil containing a mixture of the desired product and its epimer. The products were isolated by flash chromatography eluting with hexane:ethyl acetate (6:1), to yield 1.05 g of the less polar isomer (oil) and 235 mg of the more polar isomer (solid, mp 111°–112° C.) of the desired compound.

EXAMPLE 33

2,5-Anhydro-2-C-[(phenylmethoxy)methyl]-3,4,6-tris-O-(phenylmethyl)-D-glucitol

A 4.30 g portion of 2,5-anhydro-2-C-(hydroxymethyl)-3,4,6-tris-O-(phenylmethyl)-1,2$^1$-O-(phenylmethylene)-[R(and S)]-glucitol, epimeric mixture (about 3:1, less polar:more polar) was dissolved in 34 ml of dichloromethane:ether (1:1) and added to a slurry of 973 mg of lithium aluminum hydride and 3.33 g of aluminum chloride in 54 ml of the same solvent. After 25 minutes at 45°–50° C. the reaction was quenched with 13.4 ml of ethyl acetate and 26.5 ml of water. Extraction in ether gave 4.64 g of an oil containing both the glucitol and mannitol products. The isomers were separated by flash chromatography, eluting with 0.5% methanol in dichloromethane, giving 2.90 g of the desired glucitol (less polar) and 1.15 g of the more polar mannitol used in Example 42.

EXAMPLE 34

2,5-Anhydro-2-C-[(phenylmethoxy)methyl]-3,4,6-tris-O-(phenylmethyl)-D-glucitol, 1-(trifluoromethanesulfonate)

An 870 mg portion of 2,5-anhydro-2-C-[(phenylmethoxy)methyl]-3,4,6-tris-O-(phenylmethyl)-D-glucitol was dissolved in a mixture of 160 μl of pyridine and 760 μl of dichloromethane and cooled in an ice bath. A cold solution of 340 μl of triflic anhydride in 360 μl of dichloromethane was added and the mixture was stored overnight in a freezer. The mixture was diluted with ether, filtered, and the solids washed with ether. The ether solutions were combined and evaporated giving an oil which was purified by flash chromatography, eluting with hexane:ethyl acetate, giving 994 mg of the desired compound.

EXAMPLE 35

2,5-Anhydro-1-deoxy-1-(diethoxyphosphinyl)-2-C-[(phenylmethoxy)methyl]-3,4,6-tris-O-(phenylmethyl)-D-glucitol A fresh solution of sodium diethyl phosphite was prepared from sodium hydride and diethyl phosphite in tetrahydrofuran at a concentration of 2 milliequivalents/ml and added, as described below, to a solution of 260 mg of 2,5-anhydro-2-C-[(phenylmethoxy)methyl]-3,4,6-tris-O-(phenylmethyl)-D-glucitol, 1-(trifluoromethanesulfonate) in 1 ml of tetrahydrofuran. A 0.5 ml portion of the stock solution was added and the mixture stirred 1.5 hours; 0.25 ml was added and stirring continued for 2.5 hours; 0.22 ml was added, the mixture warmed to 45° C. for 20 minutes then cooled to room temperature. The mixture was worked up with hexane, ether and water, giving an oil. This oil was purified by flash chromatography, eluting with 1% methanol in dichloromethane, giving 203 mg of the desired compound.

EXAMPLE 36

2,5-Anhydro-1-deoxy-1-(diethoxyphosphinyl)-2-C-[(phenylmethoxy)methyl]-3,4-bis-O-(phenylmethyl)-D-glucitol, 6-(acetate)

A 940 mg portion of 2,5-anhydro-1-deoxy-1-(diethoxyphosphinyl)-2-C-[(phenylmethoxy)methyl]-3,4,6-tris-O-(phenylmethyl)-D-glucitol was placed in a flask under argon atmosphere. A 2.2 ml portion of acetic anhydride was added and the mixture was stirred in an ice bath. A 170 μl portion of cold boron trifluoride etherate was syringed into the mixture with stirring After 40 minutes 93 μl of cold boron trifluoride etherate was added and stirring was continued at 0° C. After a total of 1.25 hours 1.6 ml of saturated sodium bicarbonate was added and stirring was continued for 40 minutes. The mixture was evaporated, taken up in ether/water, the ether layer washed with brine, and dried, and the solvent removed. The residual oil was purified by flash chromatography, eluting with hexane:ethyl acetate (1:1), giving 620 mg of the desired compound.

EXAMPLE 37

2,5-Anhydro-1-deoxy-1-(diethoxyphosphinyl)-2-C-[(phenylmethoxy)methyl]-3,4-bis-O-(phenylmethyl)-D-glucitol A fresh solution of 2.5N ethanolic sodium ethoxide was prepared and 212 μl added to a solution of 668 mg of 2,5-anhydro-1-deoxy-1-(diethoxyphosphinyl)-2-C-[(phenylmethoxy)methyl]-3,4-bis-O-(phenylmethyl)-D-glucitol, 6-(acetate) in 2.4 ml of ethanol. After 15 minutes the reaction was quenched with 109 μl of glacial acetic acid, and the ethanol removed. The residue taken up in ether and water and the ether phase washed with saturated aqueous sodium bicarbonate and brine, dried and evaporated giving an oil which afforded 560 mg of the desired compound after chromatography.

EXAMPLE 38

2,5-Anhydro-1-deoxy-1-(diethoxyphosohinyl)-2-C-(phenylmethoxy)methyl]-3,4-bis-O-(phenylmethyl)-D-glucitol, 6-(diphenyl phosphate)

An 814 mg portion of 2,5-anhydro-1-deoxy-1-(diethoxyphosphinyl)-2-C-[(phenylmethoxy)methyl]-3,4-bis-O-(phenylmethyl)-D-glucitol was dissolved in 4 ml of pyridine in an ice bath and treated with 580 μl of diphenyl chlorophosphate as described in Example 6, giving 1.03 g of the desired compound after purification.

EXAMPLE 39

2,5-Anhydro-1-deoxy-2-C-[(phenylmethoxy)methyl]-3,4-bis-O-(phenylmethyl)-1-phosphono-D-glucitol, 6-(diphenyl phosphate)

A 511 mg portion of 2,5-anhydro-1-deoxy-1-(diethoxyphosphinyl)-2-C-[(phenylmethoxy)methyl]-3,4-bis-O-(phenylmethyl)-D-glucitol, 6-(diphenyl phosphate) was dissolved in 1.75 ml of dichloromethane and the solution treated with 250 μl of trimethylsilyl bromide as in Example 15 Evaporation gave 500 mg of the desired compound.

EXAMPLE 40

2,5-Anhydro-1-deoxy-2-C-(hydroxymethyl)-1-phosphono-D-glucitol, 6-(diphenyl phosphate)

A 517 mg portion of 2,5-anhydro-1-deoxy-2-C-[(phenylmethoxy)methyl]-3,4-bis-O-(phenylmethyl)-1-phosphono-D-glucitol, 6-(diphenyl phosphate) was hydrogenated as described in Example 16, giving 312 mg of the desired compound as an oil.

EXAMPLE 41

2,5-Anhydro-1-deoxy-2-C-(hydroxymethyl)-1-phosphono-D-glucitol, 6-(dihydrogen phosphate)

A 265 mg portion of 2,5-anhydro-1-deoxy-2-C-(hydroxymethyl)-1-phosphono-D-glucitol, 6-(diphenyl phosphate) was hydrogenated as described in Example 7, giving 180 mg of the desired product as an oil.

EXAMPLE 42

2,5-Anhydro-2-C-[(phenylmethoxy)methyl]-3,4,6-tris-O-(phenylmethyl)-D-mannitol

The fractions containing the more polar epimer from Example 33 were combined giving the desired compound.

EXAMPLE 43

2,5-Anhydro-2-C-[(phenylmethoxy)methyl]-3,4,6-tris-O-(phenylmethyl)-D-mannitol, 1-(trifluoromethanesulfonate)

A 950 mg portion of 2,5-anhydro-2-C-[(phenylmethoxy)methyl]-3,4,6-tris-O-(phenylmethyl)-D-mannitol was reacted as described in Example 34, giving 1.17 g of the desired compound which was used without purification in Example 44.

EXAMPLE 44

2,5-Anhydro-1-deoxy-1-(diethoxyphosphinyl)-2-C-[(phenylmethoxy)methyl]-3,4,6-tris-O-(phenylmethyl)-D-mannitol A 1.17 g portion of 2,5-anhydro-2-C-[(phenylmethoxy)methyl]-3,4,6-tris-O-(phenylmethyl)-D-mannitol, 1-(trifluoromethanesulfonate) was reacted as described in Example 35, giving 944 mg of the purified desired compound.

EXAMPLE 45

2,5-Anhydro-1-deoxy-1-(diethoxyphosphinyl)-2-C-[(phenylmethoxy)methyl]-3,4-bis-O-(phenylmethyl)-D-mannitol, 6-(acetate)

A 340 mg portion of 2,5-anhydro-1-deoxy-1-(diethoxyphosphinyl)-2-C-[(phenylmethoxy)methyl]-3,4,6-tris-O-(phenylmethyl)-D-mannitol was reacted as described in Example 36, giving 243 mg of the desired compound.

EXAMPLE 46

2,5-Anhydro-1-deoxy-1-(diethoxyphosphinyl)-2-C-[phenylmethoxy)methyl]-3,4-bis-O-(phenylmethyl)-D-mannitol A 544 mg portion of 2,5-anhydro-1-deoxy-1-(diethoxyphosphinyl)-2-C-[(phenylmethoxy)methyl]-3,4-bis-O-(phenylmethyl)-D-mannitol, 6-(acetate) was reacted as described in Example 37, giving 493 mg of the desired compound.

EXAMPLE 47

2,5-Anhydro-1-deoxy-1-(diethoxyphosphinyl)-2-C-(phenylmethoxy)methyl]-3,4-bis-O-(phenylmethyl)-D-mannitol, 6-(diphenyl phosphate)

A 630 mg portion of 2,5-anhydro-1-deoxy-1-(diethoxyphosphinyl)-2-C-[(phenylmethoxy)methyl]-3,4-bis-O-(phenylmethyl)-D-mannitol was reacted as described in Example 38, giving 800 mg of the desired compound.

EXAMPLE 48

2,5-Anhydro-1-deoxy-2-C-[(phenylmethoxy)methyl]-3,4-bis-O-(phenylmethyl)-1-phosphono-D-mannitol. 6-(diphenyl phosphate)

A 789 mg portion of 2,5-anhydro-1-deoxy-1-[(diethoxyphosphinyl)-2-C-[phenylmethoxy)methyl]-3,4-bis-O-(phenylmethyl)-D-mannitol, 6-(diphenyl phosphate) was dealkylated as described in Example 39, giving 707 mg of the desired compound.

EXAMPLE 49

2-5-Anhydro-1-deoxy-2-C-(hydroxymethyl)-1-phosphono-D-mannitol, 6-(diphenyl phosphate)

A 570 mg portion of 2,5-anhydro-1-deoxy-2-C-[(phenylmethoxy)methyl]-3,4-bis-O-(phenylmethyl)-1-phosphono-D-mannitol, 6-(diphenyl phosphate) was hydrogenated as described in Example 16, giving 370 mg of the desired compound.

EXAMPLE 50

2,5-Anhydro-1-deoxy-2-C-(hydroxymethyl)-1-phosphono-D-mannitol, 6-(dihydrogen phosphate)

A 330 mg portion of 2,5-anhydro-1-deoxy-2-C-(hydroxymethyl)-1-phosphono-D-mannitol, 6-(diphenyl phosphate) was hydrogenated as described in Example 7, giving 277 mg of the desired product as an oil.

EXAMPLE 51

1-Deoxy-1-(diethoxyphosphinyl)-3,4,6-tris-O-(phenylmethyl)-D-fructofuranose

To a stirred solution of 15.6 ml of 1.6M n-butyllithium in hexane and 20 ml of tetrahydrofuran at −78° C., was added a solution of 3.80 g of diethyl methylphosphonate in 10 ml of tetrahydrofuran during 10 minutes. After 15 minutes at −78° C., a solution of 4.18 g of 2,3,5-tris-O-(phenylmethyl)-D-arabinonic acid, qamma-lactone [Y. Rabinsohn & H. G. Fletcher, *J. Org. Chem.*, 32, 3452–3457 (1967)] in 15 ml of tetrahydrofuran was added during 5 minutes. After 30 minutes at −78° C. the solution was warmed to 0° C. during 5 minutes, stirred at 0° C. for 2 minutes, recooled to −78° C. and quenched with 3.0 ml of glacial acetic acid. The mixture was partitioned with dichloromethane-water. The organic layer was washed successively with water, sodium bicarbonate solution, water and brine, dried and concentrated. The residue was subjected to column chromatography on silica gel (ethyl acetate-heptane) giving the desired compound as an oil, CMR δ 101.2 and 104.3 (doublets, corresponding to anomeric carbon of minor and major anomer, respectively).

EXAMPLE 52

2,5-Anhydro-1-deoxy-1-(diethoxyphosphinyl)-3,4-bis-O-(phenylmethyl)-D-arabino-hex-1-enitol, 6-acetate, (E) and (Z) isomers To a stirred solution of 5.71 g of 1-deoxy-1-(diethoxyphosphinyl)-3,4,6-tris-O-(phenylmethyl)-D-fructofuranose in 15 ml of acetic anhydride at 0° C. was added 1.47 ml of boron trifluoride etherate during 2 minutes. After 4 days at 0° C. the solution was stirred vigorously, with ice bath cooling, with saturated sodium bicarbonate solution. The mixture was extracted with ether. The extract was washed successively with water and brine, dried and concentrated. The residue was subjected to column chromatography on silica gel, giving the desired compound as a mixture:minor, mobile E-isomer, oil, CMR δ 86.8 (doublet, J=205 Hz, =CH-P); major, polar Z-isomer, oil, CMR δ 85.5 (doublet, J=194 Hz,=CH-P).

EXAMPLE 53

1-Deoxy-1-(diethoxyphosphinyl)-3,4-bis-O-(phenylmethyl)-D-fructofuranose, 6-acetate To a stirred solution of 0.25 g of 2,5-anhydro-1-deoxy-1-(diethoxyphosphinyl)-3,4-bis-O-(phenylmethyl)-D-arabino-hex-1-enitol, 6-acetate in 5.0 ml of dichloromethane saturated with water, was added 0.31 ml of trifluoracetic acid. The solution was stirred at 25° C. for 18 hours, then partitioned with ether-sodium bicarbonate solution. The organic layer was washed with water and brine, dried and concentrated. The residue was subjected to chromatography on silica gel (ethyl acetate-heptane) giving the desired compound as an oil, CMR δ 101.4 and 104.4 (doublets, corresponding to anomeric carbon of minor and major anomer respectively.

EXAMPLE 54

1-Deoxy-1-(diethoxyphosphinyl)-3,4-bis-O-(phenylmethyl-D-fructofuranose

Following the procedure of Example 37, treatment of 1-deoxy-1-(diethoxyphosphinyl)-3,4-bis-O-(phenylmethyl)-D-fructofuranose, 6-acetate with ethanolic sodium ethoxide provides the desired compound.

EXAMPLE 55

1-Deoxy-1-(diethoxyphosphinyl)-3,4-bis-O-(phenylmethyl)-D-fructofuranose, 6-(diphenyl phosphate)

Following the procedure of Example 38, treatment of !-deoxy-1-(diethoxyphosphinyl)-3,4-bis-O-(phenylmethyl)-D-fructofuranose with diphenyl chlorophosphate in pyridine provides the desired compound.

EXAMPLE 56

1-Deoxy-1-phosphono-D-fructofuranose, 6-(dihydrogen phosphate)

Following the procedure of Example 39, treatment of 1-deoxy-1-(diethoxyphosphinyl)-3,4-bis-O-(phenylmethyl)-D-fructofuranose, 6-(diphenyl phosphate) with trimethylsilyl bromide, followed by hydrogenolysis in the presence of palladium hydroxide, followed by hydrogenolysis in the presence of platinum provides the desired product.

We claim:

1. A compound selected from those of the formula:

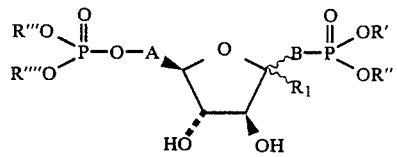

wherein A and B are selected independently of each other from the group consisting of $C_1$ to $C_4$ alkylene and $C_2$ to $C_4$ hydroxyalkylene $R_1$ is selected from the group consisting of hydrogen, hydroxy, $C_1$ to $C_4$ alkyl, $C_1$ to $C_4$ hydroxyalkyl, $C_2$ to $C_4$ dihydroxyalkyl, $C_3$ or $C_4$ trihydroxyalkyl and $C_4$ tetrahydroxyalkyl; R', R", R''' and R'''' are selected independently from the group consisting of hydrogen, $C_1$ to $C_{18}$ alkyl, $C_3$ to $C_6$ cycloalkyl, phenyl, mono- and disubstituted phenyl (wherein the substituents are selected from alkyl $C_1$ to $C_6$, alkoxy $C_1$–$C_6$, $NO_2$ or halo), $C_3$ to $C_8$ isoalkyl, $Cl_3CCH_2$—, $CH_2$=$CHCH_2$—, $ZCH_2CH_2$— (where Z is $SO_2R_2$, $SR_2$, $OR_2$ or $Si(R_2)_3$ and $R_2$ is $C_1$ to $C_3$ alkyl),

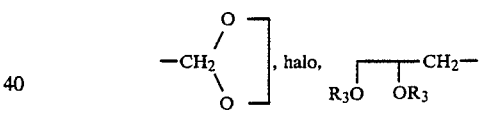

where $R_3$ is $C_1$ to $C_3$ alkyl and $R_3$–$R_3$ is alkylene or acetal),

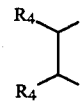

where $R_4$ is hydrogen or methyl),

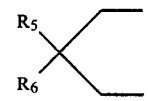

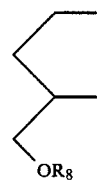

(where $R_8$ is hydrogen or $C_1$ to $C_{18}$ alkyl,

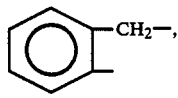

phenylmethyl, substituted phenylmethyl wherein the substituents are selected from $C_1$ to $C_{18}$ alkyl, $C_1$ to $C_6$ alkoxy, nitro and halogen; and with the provisos that (a) when A and B are both —$CH_2$— and R', R", R'" and R"" are the same and are phenyl or ethyl, then $R_1$ may not be hydrogen, and (b) when A and B are both —$CH_2$— and R', R", R'" and R"" are hydrogen, then $R_1$ may not be hydrogen or —$CH_2OH$; and, when any one or more of R', R", R'", or R"" are hydrogen, the pharmaceutically acceptable salts thereof.

2. The compound according to claim 1, 4,7-anhydro-1,2,3-trideoxy-1-(diphenoxyphosphinyl)-D-glucooctitol, 8-(diphenyl phosphate).

3. The compound according to claim 1, 4,7-anhydro-1,2,3-trideoxy-1-(diphenoxyphosphinyl)-D-mannooctitol, 8-(diphenyl phosphate).

4. The compound according to claim 1, 2,5-anhydro-1-deoxy-1-phosphono-D-mannitol, 6-(diphenyl phosphate).

5. The compound according to claim 1, 2,5-anhydro-1-deoxy-1-phosphono-D-glucitol, 6-(diphenyl phosphate).

6. The compound according to claim 1, 3,6-anhydro-1,2-dideoxy-1-(diphenoxyphosphinyl)-D-mannoheptitol, 7-(diphenyl phosphate).

7. The compound according to claim 1, 3,6-anhydro-1,2-dideoxy-1-(diphenoxyphosphinyl)-D-glucoheptitol, 7-(diphenyl phosphate).

8. The compound according to claim 1, 2,5-anhydro-1-deoxy-2-C-(hydroxymethyl)-1-phosphono-D-glucitol, 6-(diphenyl phosphate).

9. The compound according to claim 1, 2,5-anhydro-2-C-(phosphonomethyl)-D-mannitol, 6-(diphenyl phosphate).

10. The compound according to claim 1, 4,7-anhydro-1,2,3-trideoxy-1-(dihydroxyphosphinyl)-D-glucooctitol, 8-(dihydrogen phosphate).

11. The compound according to claim 1, 4,7-anhydro-1,2,3-trideoxy-1-(dihydroxyphosphinyl)-D-mannooctitol, 8-(dihydrogen phosphate).

12. The compound according to claim 1, 3,6-anhydro-1,2-dideoxy-1-phosphono-D-manno-heptitol, 7-(dihydrogen phosphate).

13. The compound according to claim 1, 3,6-anhydro-1,2-dideoxy-1-phosphono-D-gluco-heptitol, 7-(dihydrogen phosphate).

14. The compound according to claim 1, 1-deoxy-1-phosphono-D-fructofuranose, 6-(dihydrogen phosphate).

15. The method of treating hyperglycemia in a mammal in need of such treatment which comprises administering to said mammal a therapeutically effective amount of a compound selected from those of claim 1.

16. The method of treating diabetes in a mammal in need of such treatment which comprises administering to said mammal a therapeutically effective amount of a compound selected from those of claim 1.

17. A pharmaceutical composition which comprises a therapeutically effective amount of a compound selected from those of claim 1 in association with a pharmaceutically acceptable carrier.

* * * * *